(12) United States Patent
Globerman et al.

(10) Patent No.: US 12,226,948 B2
(45) Date of Patent: Feb. 18, 2025

(54) DEVICES, ASSEMBLIES, KITS, SYSTEMS AND METHODS FOR SHAPING OF ELONGATED ELEMENTS CONTAINING THERMOPLASTIC POLYMERS

(71) Applicants: CarboFix Spine Inc, Ocean Isle Beach, NC (US); Oren Globerman, Kfar-Shmaryahu (IL)

(72) Inventors: Oren Globerman, Kfar-Shmaryahu (IL); Mordechay Beyar, Tel Aviv (IL); Daniel Umansky, Kfar Saba (IL)

(73) Assignee: CarboFix Spine Inc., NC (US)

( * ) Notice: Subject to any disclaimer, the term of this patent is extended or adjusted under 35 U.S.C. 154(b) by 507 days.

(21) Appl. No.: 17/435,786

(22) PCT Filed: Mar. 5, 2020

(86) PCT No.: PCT/IL2020/050261
§ 371 (c)(1),
(2) Date: Sep. 2, 2021

(87) PCT Pub. No.: WO2020/178838
PCT Pub. Date: Sep. 10, 2020

(65) Prior Publication Data
US 2022/0048240 A1     Feb. 17, 2022

Related U.S. Application Data

(60) Provisional application No. 62/814,873, filed on Mar. 7, 2019.

(51) Int. Cl.
*B29C 53/08* (2006.01)
*A61B 17/68* (2006.01)
(Continued)

(52) U.S. Cl.
CPC ............ *B29C 53/083* (2013.01); *A61B 17/68* (2013.01); *B29C 53/84* (2013.01);
(Continued)

(58) Field of Classification Search
CPC .................... B29C 53/083; B21D 7/03; A61B 2017/00526
See application file for complete search history.

(56) References Cited

U.S. PATENT DOCUMENTS 3,952,572 A * 4/1976 Mergler ................... B21D 7/02
72/308
5,405,073 A * 4/1995 Porter .................. A61B 17/072
227/19

(Continued)

FOREIGN PATENT DOCUMENTS

CN     1215635      5/1999
CN     2334512      8/1999
(Continued)

OTHER PUBLICATIONS

Office Action of Chinese Application No. 2020800340384 mailed on Feb. 13, 2023.
(Continued)

*Primary Examiner* — Andrew D Graham
(74) *Attorney, Agent, or Firm* — PEARL COHEN ZEDEK LATZER BARATZ LLP

(57) ABSTRACT

Devices, assemblies, kits, systems and methods for shaping of elongated elements containing thermoplastic polymers are disclosed.

6 Claims, 32 Drawing Sheets

(51) Int. Cl.
*B29C 53/84* (2006.01)
*A61B 17/00* (2006.01)
*B29K 101/12* (2006.01)
*B29L 31/00* (2006.01)

(52) U.S. Cl.
CPC . *A61B 2017/00526* (2013.01); *B29K 2101/12* (2013.01); *B29L 2031/7532* (2013.01)

(56) References Cited

U.S. PATENT DOCUMENTS

| | | | | |
|---|---|---|---|---|
| 5,475,073 | A * | 12/1995 | Guo | C08F 216/1416 |
| | | | | 526/329 |
| 5,554,253 | A * | 9/1996 | Watanabe | B29C 66/7373 |
| | | | | 604/905 |
| 5,938,662 | A | 8/1999 | Rinner | |
| 8,298,242 | B2 | 10/2012 | Justis et al. | |
| 9,155,492 | B2 * | 10/2015 | Jenkins | A61B 5/065 |
| 9,901,705 | B2 | 2/2018 | Armour et al. | |
| 2004/0267260 | A1 * | 12/2004 | Mack | A61B 17/7028 |
| | | | | 606/907 |
| 2009/0054932 | A1 | 2/2009 | Butler et al. | |
| 2009/0326582 | A1 | 12/2009 | Songer et al. | |
| 2010/0101295 | A1 * | 4/2010 | Miller | B29C 53/083 |
| | | | | 72/364 |
| 2010/0318130 | A1 | 12/2010 | Parlato et al. | |
| 2011/0259075 | A1 * | 10/2011 | Kirchmer | B21D 7/0225 |
| | | | | 72/389.1 |
| 2011/0265538 | A1 * | 11/2011 | Trieu | B21D 7/066 |
| | | | | 72/295 |
| 2011/0270262 | A1 * | 11/2011 | Justis | A61B 17/8863 |
| | | | | 606/101 |
| 2012/0101480 | A1 * | 4/2012 | Ingle | B29C 53/821 |
| | | | | 156/190 |
| 2014/0074141 | A1 * | 3/2014 | Johnson | A61M 25/10182 |
| | | | | 606/192 |
| 2016/0001039 | A1 | 1/2016 | Armour et al. | |
| 2016/0110139 | A1 | 1/2016 | Armour | |
| 2017/0239877 | A1 * | 8/2017 | Lin | B29C 53/083 |
| 2018/0117290 | A1 * | 5/2018 | Matlock | A61M 29/02 |
| 2020/0138422 | A1 * | 5/2020 | Hebert | B29D 23/00 |
| 2020/0139082 | A1 * | 5/2020 | Matlock | B29C 48/34 |

FOREIGN PATENT DOCUMENTS

| | | |
|---|---|---|
| CN | 1872441 | 12/2006 |
| CN | 107097401 | 8/2017 |
| JP | 2006150934 | 6/2006 |
| WO | WO-2016/088130 A1 | 6/2016 |

OTHER PUBLICATIONS

Partial Search Report of EP Application No. 20766874.0 mailed on Oct. 28, 2022.
International Search Report and Written Opinion for PCT Application No. PCT/IL2020/050261, mailed on Jun. 30, 2020.

* cited by examiner

800

Front view
Side view

Front view:

Side view:

Front view:

US 12,226,948 B2

DEVICES, ASSEMBLIES, KITS, SYSTEMS AND METHODS FOR SHAPING OF ELONGATED ELEMENTS CONTAINING THERMOPLASTIC POLYMERS

CROSS-REFERENCE TO RELATED APPLICATIONS

This application is a National Phase Application of PCT International Application No. PCT/IL2020/050261, International Filing Date Mar. 5, 2020, claiming the benefit of U.S. Provisional Patent Application No. 62/814,873, filed Mar. 7, 2019, both of which are hereby incorporated by reference in their entireties

FIELD OF THE INVENTION

The present invention relates to the field of devices for curving elongated elements and, more particularly, to devices for curving elongated elements containing thermoplastic polymers.

BACKGROUND OF THE INVENTION

An elongated element containing thermoplastic polymers must be heated in order to be shaped. Shaping of the heated elongated element may undesirably distort a cross-sectional profile of the elongated element in a shaping region.

SUMMARY OF THE INVENTION

Some embodiments of the present invention may provide a device for maintaining the shape of a transverse cross-sectional profile of an elongated orthopedic implant during a shaping thereof, which device may include: multiple coils adjacently arranged along a longitudinal axis of the device and helically connected with each other, wherein the coils are adapted to surround and tightly support at least a portion of the elongated orthopedic implant and are unwindably removable from the elongated orthopedic implant upon the shaping thereof.

In some embodiments, the coils are shaped and dimensioned to ensure that gaps between adjacent coils formed on a convex side of the device upon bending of the elongated orthopedic implant do not exceed a predetermined gap threshold.

In some embodiments, the coils are made of a metal wire having a rectangular cross-section, wherein the rectangular cross-section has a first dimension along the longitudinal axis of the device and a second dimension that is perpendicular to the first dimension.

In some embodiments, the first dimension ranges between 0.1-3.0 mm.

In some embodiments, the second dimension ranges between 0.05-0.3 mm.

In some embodiments, the predetermined gap threshold is no more than 0.5 mm.

In some embodiments, the coils are made of an elastic material so as to enable at least one of: a desired measure of relative motion of the coils with respect to each other along a direction that is parallel to at least one of: the longitudinal axis of the device and an axis that is perpendicular to the longitudinal axis of the device, and a desired measure of deformation of the coils in the directions that are perpendicular to the longitudinal axis of the device.

In some embodiments, dimensions of a transverse cross-section of the device are smaller than dimensions of the transverse cross-sectional profile of the elongated orthopedic implant to be used with the device.

In some embodiments, the device may include: a first stopper adapted to removably affix a first end of the device to the elongated orthopedic implant, and a second stopper adapted to removably affix a second end of the device to the elongated orthopedic implant, wherein the affixing of the first end and the second end of the device to the elongated orthopedic implant prevent at least one of undesired winding and unwinding and axial sliding of the device during shaping of the elongated orthopedic implant.

Some embodiments of the present invention may provide an assembly for maintaining a shape of a transverse cross-sectional profile of an elongated orthopedic implant, which assembly may include: a first device as described above, wherein the first device is adapted to surround and tightly support at least a portion of the elongated orthopedic implant, and a second device as described above, wherein the second device is adapted to surround and tightly support at least a portion of the first device such that the coils of the second device overlap with regions of contact between the coils of the first device.

Some embodiments of the present invention may provide an assembly for maintaining a shape of a transverse cross-sectional profile of an elongated orthopedic implant, which assembly may include: a device as described above, and an envelope made of an elastic material and adapted to accommodate the device and the elongated orthopedic implant.

In some embodiments, the envelope may include a tube adapted to tightly surround the device.

In some embodiments, the tube may include an indent on an external surface thereof and along at least a portion of a length thereof.

In some embodiments, the envelope may include a bellow tube, wherein the bellow tube covers at least a portion of the elongated orthopedic implant when it is inserted to a rest place within the bellow tube.

In some embodiments, the envelope may include a cap adapted to close a first end of the bellow tube, wherein a second end of the bellow tube is a closed end, wherein the cap may include first cap part and a second cap part screwable onto the first cap part.

In some embodiments, the envelop may include: a first cap adapted to close a first end of the bellow tube, wherein the first cap may include a proximal first-cap part and a distal first-cap part screwable onto the proximal first-cap part, and a second cap adapted to close a second end of the bellow tube.

Some embodiments of the present invention may provide a device for bending of an elongated assembly, which device may include: a housing, and multiple bending units partly disposed within the housing at a distance with respect to each other, wherein each of the multiple bending units may include: a receiving member adapted to receive a portion of the elongated assembly, the receiving member being movable between an initial position and at least one other position, and a driving assembly adapted to move the receiving member, wherein the receiving members of the multiple bending units are aligned in a reference plane and along a reference longitudinal axis when in their respective initial positions and are movable in at least one of: a first direction that is parallel to the reference plane and a second direction that is perpendicular to the first direction.

In some embodiments, the elongated assembly may include at least one of: an elongated orthopedic implant at least partly surrounded by a transverse cross-sectional profile maintaining device, and an envelope enveloping at least a portion of an elongated orthopedic implant at least partly surrounded by a transverse cross-sectional profile maintaining device.

In some embodiments, the transverse cross-sectional profile maintaining device may include: multiple coils adjacently arranged along a longitudinal axis of the device and helically connected with each other, wherein the coils are adapted to surround and tightly support at least a portion of the elongated orthopedic implant and are unwindably removable from the elongated orthopedic implant upon the shaping thereof.

In some embodiments, the envelope may include a bellow tube, the bellow tube covers at least a portion of the elongated orthopedic implant when it is inserted to a rest place within the bellow tube.

In some embodiments, the envelope may include a cap adapted to close a first end of the bellow tube, and wherein a second end of the bellow tube is a closed end, the cap may include a first cap part and a second cap part screwable onto the first cap part.

In some embodiments, the envelope may include: a first cap adapted to close a first end of the bellow tube, wherein the first cap may include a proximal first-cap part and a distal first-cap part screwable onto the proximal first-cap part, and a second cap adapted to close a second end of the bellow tube.

In some embodiments, each of the receiving members is rotatable about a central axis thereof.

In some embodiments, each of the bending units may include: a mover movable between an initial mover position and at least one other mover position, wherein a position of the mover defines a measure of movement of the receiving member of the respective bending unit.

In some embodiments, the driving assembly of each of the bending units may include: a first rail coupled at its ends to the housing in a plane that is parallel to reference plane, wherein the receiving member of the respective bending unit is slidably coupled to the first rail, a rotatable arm pivotally coupled at its first end to an end of the receiving member of the respective bending unit, an actuation arm pivotally coupled at its first end to a second end of the rotatable arm, the second arm being movable in a plane that is parallel to the reference plane between an initial position and an extended position, a second rail coupled at its ends to the housing, the second rail being parallel to the rotatable arm when the actuation arm is in the extended position, wherein the mover of the respective bending unit is slidably coupled to the second rail, and a rotational axis arm coupled at its first end to the mover of the respective bending unit and movably coupled at its second end to the rotatable arm, wherein a position of the second end of the rotational axis arm dictated by the position of the mover of the respective bending unit defines a rotational axis about which the rotational arm rotates upon actuation and thus defines the measure of movement of the receiving member of the respective bending unit, wherein movement of the actuation arm of the driving assembly between the extended position and the initial positions moves the second end of the rotatable arm, thereby rotating the rotatable arm about the rotational axis defined by the second end of the rotational axis arm and moving the receiving member of the respective bending unit along the first rail between the initial position and one of the at least one another position thereof.

In some embodiments, the second ends of the actuation arms of the driving assemblies of the bending units are connected using an actuation rod, such that movement of the actuation rod causes simultaneous movement of the actuation arms of the driving assemblies of the bending units.

In some embodiments, each of the bending units may include a rotatable rod rotatably coupled at its ends to the housing in a plane that is parallel to reference plane, wherein the receiving member of the respective bending unit is movably coupled to the rod and is adapted to move along the rod when the rod rotates, and the driving assembly of each of the bending units may include a motor and a transmission sub-unit for transmitting rotational motion generated by the motor to the rotatable rod to thereby move the receiving member of the respective bending unit between the initial position and one of the at least one another position thereof.

In some embodiments, at least the receiving members of the bending units are removably couplable to the driving assemblies thereof.

In some embodiments, the device may include a controller configured to: receive a desired bending profile of the elongated assembly, and control the operation of the driving assemblies of the bending units to move the receiving members of the bending units according to the desired bending profile of the elevated assembly.

Some embodiments of the present invention may provide a device for heating an elongated assembly, which device may include: a housing having an interior adapted to receive the elongated assembly, and two or more heating elements at least partly enveloping the housing along at least a portion thereof.

In some embodiments, the device may include a heating envelope adapted to receive the elongated assembly and adapted to be positioned within the interior of the housing.

In some embodiments, the two or more heating elements are battery-operated.

Some embodiments of the present invention may provide a system for heating and bending of an elongated assembly, which system may include: a device for heating the elongated assembly as described above, and a device for bending an elongated assembly as described above.

Some embodiments of the present invention may provide a method of bending of an elongated assembly, which method may include: providing an elongated assembly that may include an elongated orthopedic implant at least partly surrounded by a transverse cross-sectional profile maintaining device, heating the elongated assembly using a heating device to provide a heated elongated assembly, configuring a bending device according to a desired bending profile of the elongated orthopedic implant, bending the heated elongated assembly by the bending device to provide a bended elongated assembly including a bended elongated orthopedic implant having the desired bending profile, cooling the bended elongated assembly, and releasing the transverse cross-sectional profile maintaining device from the bended elongated orthopedic implant.

In some embodiments, the elongated assembly, the heating device and the bending device are sterile.

In some embodiments, at least one of the heating device and the bending device is not sterile and wherein the elongated assembly may include an envelope that at least partly envelopes the sterile elongated orthopedic implant at least partly surrounded by sterile transverse cross-sectional profile maintaining device.

In some embodiments, the transverse cross-sectional profile maintaining device may include: multiple coils adjacently arranged along a longitudinal axis of the device and helically connected with each other, wherein the coils are adapted to surround and tightly support at least a portion of the elongated orthopedic implant and are unwindably removable from the elongated orthopedic implant upon the shaping thereof.

In some embodiments, the envelope may include a bellow tube, wherein the bellow tube covers at least a portion of the elongated orthopedic implant when it is inserted to a rest place within the bellow tube.

In some embodiments, the envelope may include a cap adapted to close a first end of the bellow tube and wherein a second end of the bellow tube is a closed end, wherein the cap may include first cap part and a second cap part screwable onto the first cap part.

In some embodiments, the envelope may include: a first cap adapted to close a first end of the bellow tube, wherein the first cap may include a proximal first-cap part and a distal first-cap part screwable onto the proximal first-cap part, and a second cap adapted to close a second end of the bellow tube.

These, additional, and/or other aspects and/or advantages of the present invention are set forth in the detailed description which follows, possibly inferable from the detailed description, and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

Figure 1A:
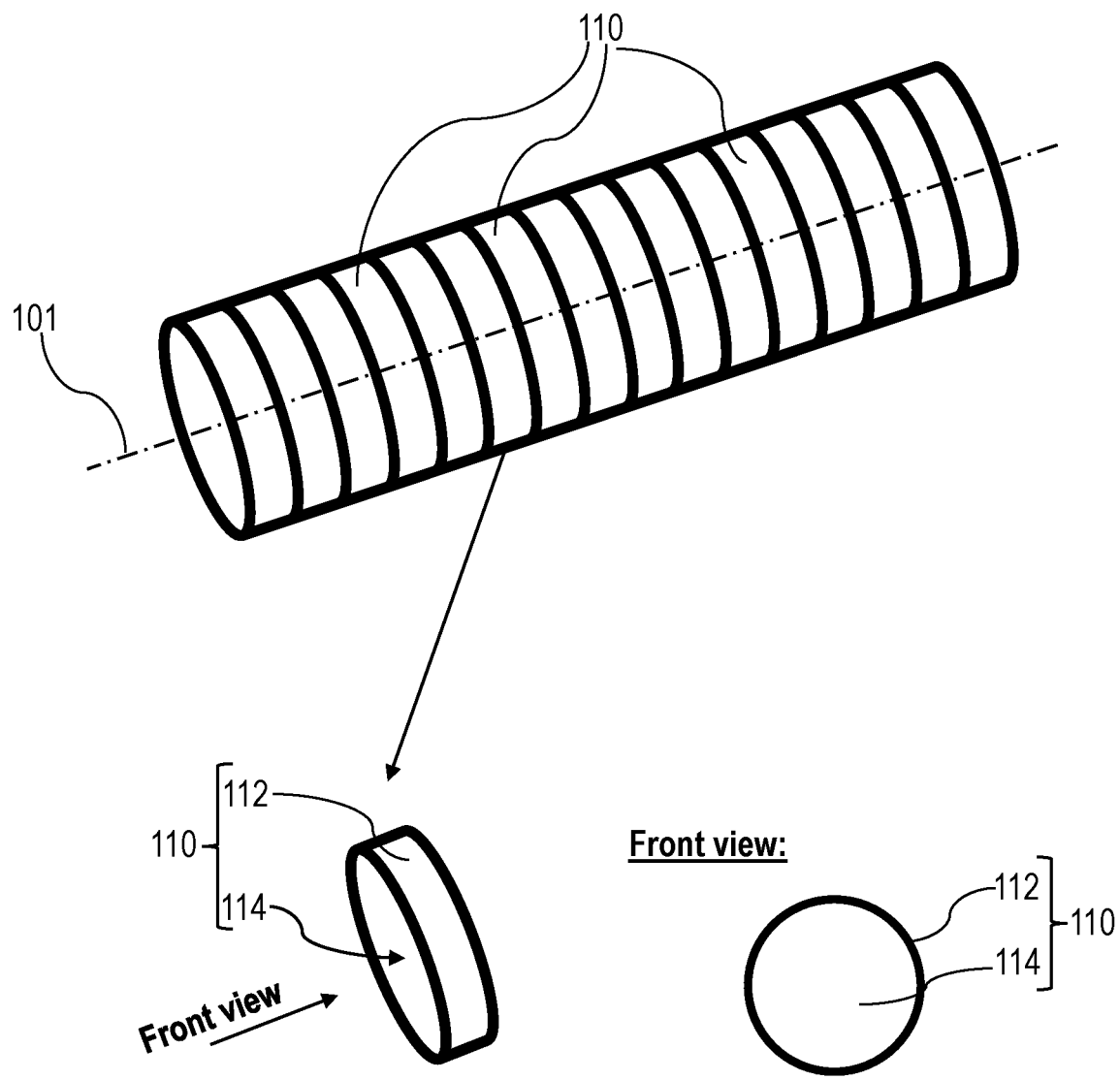
FIGS. 1A, 1B, 1C, 1D and 1E are schematic illustrations of a device for maintaining a shape of a transverse cross-sectional profile of an elongated element, according to some embodiments of the invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that, throughout the specification, discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Generally, devices, systems, kits and methods for shaping of an elongated element are disclosed.

The term "elongated element" as used herein below relates to any elongated object that contains one or more thermoplastic polymers. For example, the elongated element may contain a polyether ether ketone (PEEK) polymer. In another example, the elongated element may contain about 60% carbon and about 40% PEEK polymer.

In some embodiments, the elongated element is an orthopedic implant. For example, the elongated element may be any one from a list including an orthopedic rod (e.g., for a pedicle screw assembly), orthopedic plate (e.g., femur plate, humerus plate, etc.), K-Wire, orthopedic nails (e.g., humerus nail, cephalomedullary nail, etc.), etc.

The elongated element containing thermoplastic polymer(s) should be heated or pre-heated in order to be shaped. Shaping of the elongated element may be any mechanical action intended to change an initial shape of the elongated element. For example, the shaping may include any or a combination of bending, twisting, stretching and/or compression of the elongated element. The description below provides bending as an example for shaping. It is noted that the devices, systems, kits and methods described below may be also utilized for other types or combination of shaping (e.g., such as twisting, stretching and/or compression).

Shaping of heated elongated element may, for example, distort a cross-sectional profile of elongated element, for example in a shaping region. For example, when heated elongated element having an initial circular cross-section (e.g., rod) is being bent, the cross-sectional profile of the elongated element in a bending region may be distorted and may change from circular to, for example, oval or elliptic.

The disclosed devices, systems, kits and methods may enable shaping of the elongated elements containing thermoplastic polymers while preventing distortion of the shape of the cross-sectional profile in the shaping region. Furthermore, the disclosed devices and systems may be located in the operation room and may enable shaping of the elongated elements thereof in the operation room during the operational procedure.

Reference is now made to FIGS. 1A, 1B, 1C, 1D and 1E, which are schematic illustrations of a device 100 for maintaining a shape of a transverse cross-sectional profile of an elongated element 90, according to some embodiments of the invention.

According to some embodiments, device 100 includes multiple members 110 (e.g., as shown in FIGS. 1A, 1B, 1C, 1D and 1E). Members 110 may be arranged along a longitudinal axis 101 of device 100. Members 110 may be adjacent to each other (e.g., may touch each other). Members 110 may be arranged along longitudinal axis 101 in a way that enables a desired measure of relative motion (e.g., lateral motion, longitudinal motion and/or angled motion) of members 110 with respect to each other.

Each of multiple members 110 may include a peripheral member portion 112 that may at least partly surround a central member opening 114 of respective member 110 (e.g., as shown in FIG. 1A).

Figure 1B:
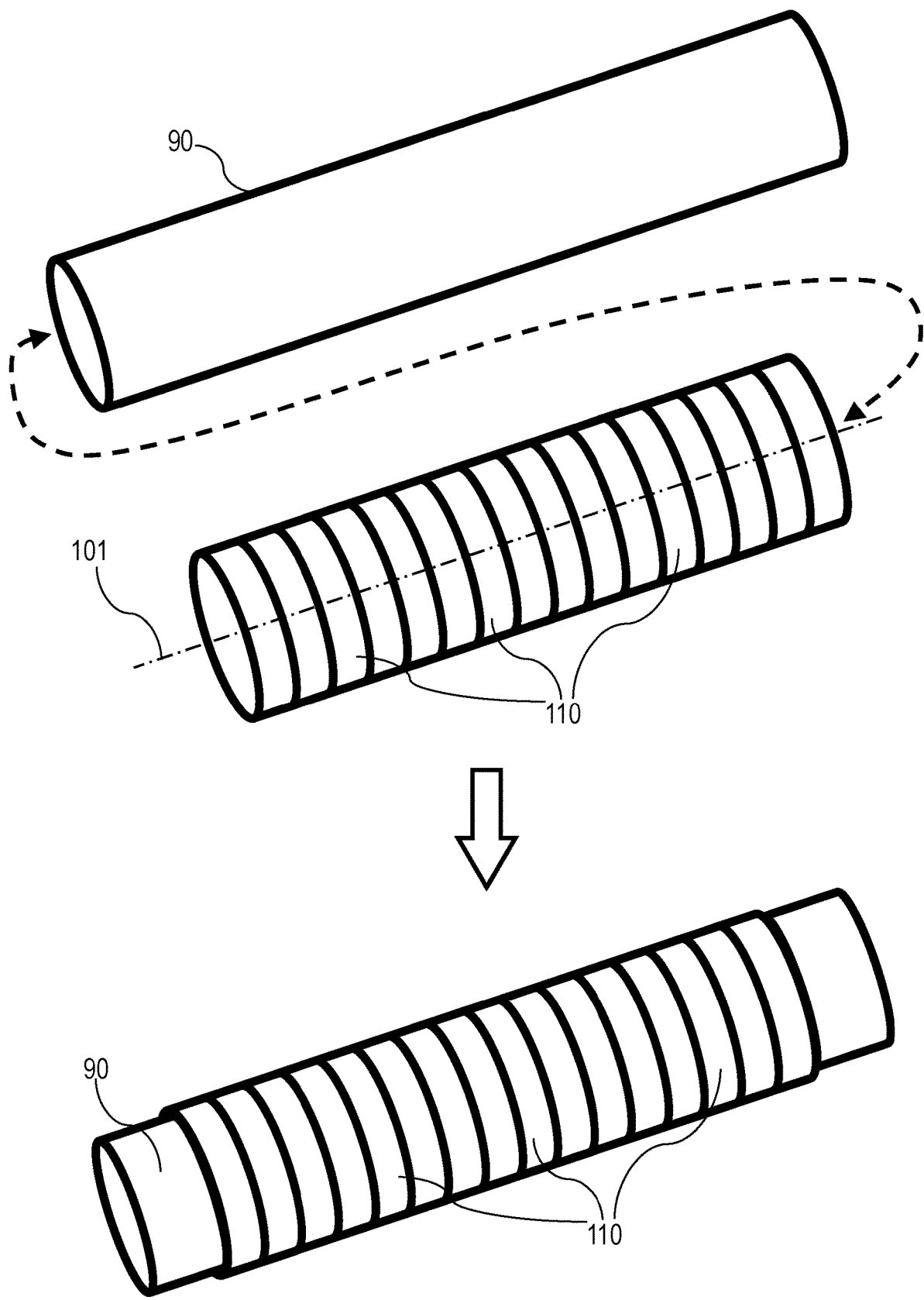

According to various embodiments, members 110 may be threaded onto elongated element 90 or elongated element 90 may be inserted through central member openings 114 of members 110 such that each of members 110 surrounds and tightly supports a corresponding portion of elongated element 90 (e.g., as indicated by dashed arrow in FIG. 1B).

Figure 1C:
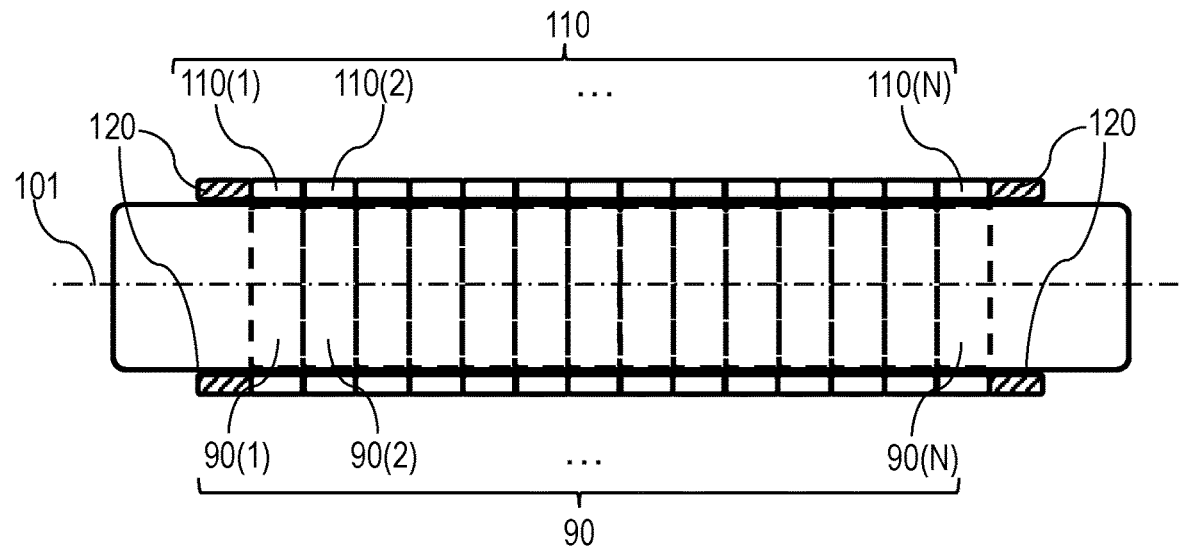

For example, a first member 110(1) may receive and tightly support a first portion 90(1) of elongated element 90, a second member 110(2) may receive and tightly support a second portion 90(2) of elongated element 90, and/or an N-th member 110(N) may receive and tightly support an N-th portion 90(N) of elongated element 90 (e.g., as shown in FIG. 1C).

Shape and dimensions of members 110 and/or of peripheral member portions 112 and/or of central member openings 114 of members 110 may mate with the shape and dimensions of, for example, cross-sectional profile of the corresponding portions of elongated element 90 to provide the tight receipt and support of elongated element 90 therein.

According to some embodiments, elongated element 90 supported within device 100 is heated (or pre-heated) such that a temperature of elongated element 90 is elevated up to a predetermined temperature value (e.g., as described below with respect to FIG. 5). In some embodiments, the predetermined temperature value is 380° C. Members 110 of device 100 may be made of a material that does not undergo thermal deformation at the predetermined temperature value thereof. Members 110 may be made of biocompatible material. For example, members 110 may be made of stainless steel or titanium.

According to some embodiments, device 100 enables bending elongated element 90 while preventing distortion/change of the cross-sectional profile of elongated element 90 in the bending region.

Figure 1D:
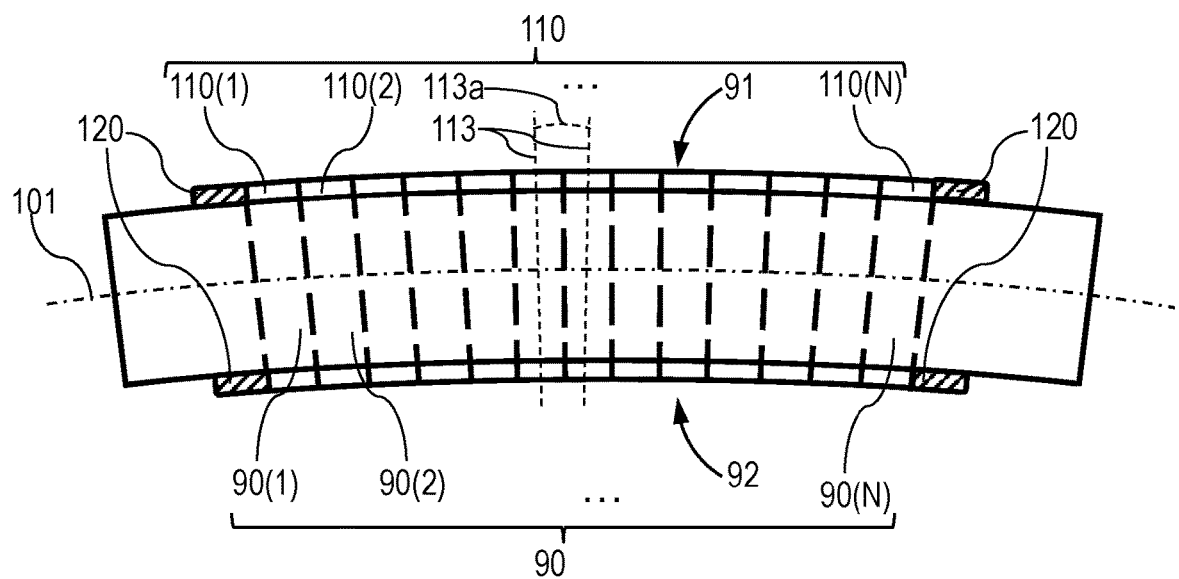

When bending forces are applied to elongated element 90 supported within device 100, members 110 may move with respect to each other, e.g., by getting farther or closer to each other or by changing the relative angle 113a between planes 113 of two adjacent members, while remaining unmovable (or substantially unmovable) with respect to the corresponding portions of elongated element 90 (e.g., due to tight support thereof, as described above), thereby allowing bending of elongated element 90 (e.g., as shown in FIG. 1D). Members 110 do not deform (or substantially do not deform) during bending (as members 110 may move with respect to each other and do not undergo thermal deformation), thereby preventing distortion of the cross-sectional profile of the corresponding portion of elongated element 90 and thereby maintaining (or substantially maintaining) the shape of the cross-sectional profile of elongated element 90 along the entire bending region.

According to some embodiments, device 100 includes one or more stoppers 120 (e.g., as shown in FIGS. 1C and 1D). Stoppers 120 may, for example, affix first member 110(1) and N-th member 110(N) at both ends of device 100 to, for example, further secure first member 110(1) and N—the member 110(N) in their respective positions and prevent sliding of the members thereof, for example, during bending of elongated element 90.

Figure 1E:
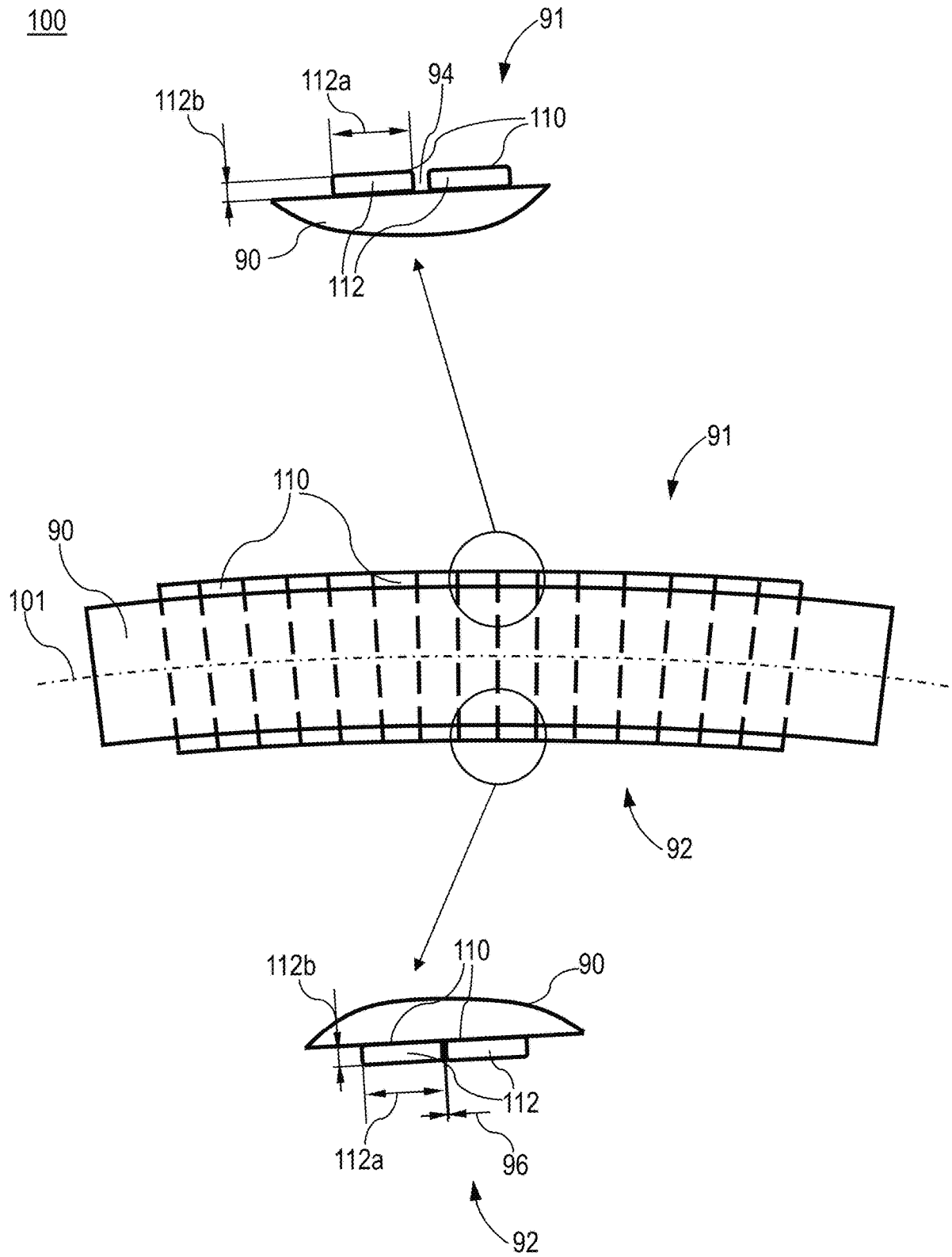
Figure 2A:
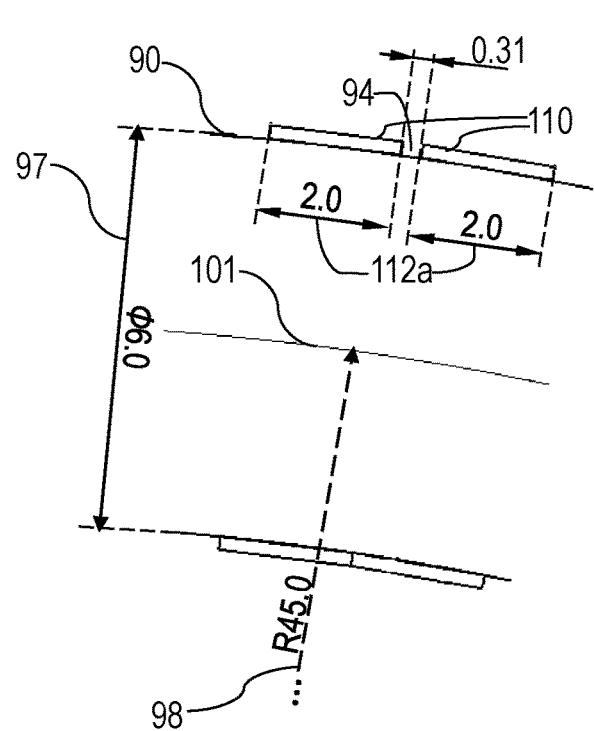
FIGS. 2A, 2B, 2C, 2D, 2E and 2F are schematic illustrations of various configurations of members of a device for maintaining a shape of a transverse cross-sectional profile of an elongated element, according to some embodiments of the invention.
Figure 2B:
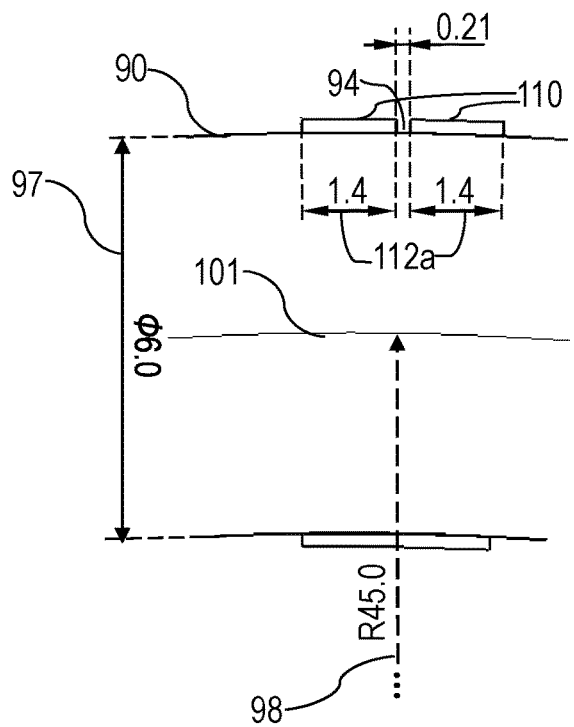
Figure 2C:
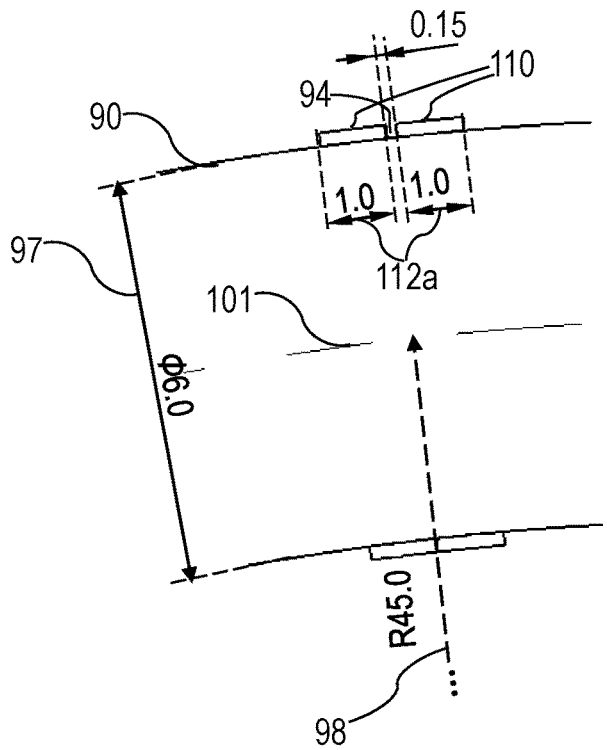
Figure 2D:
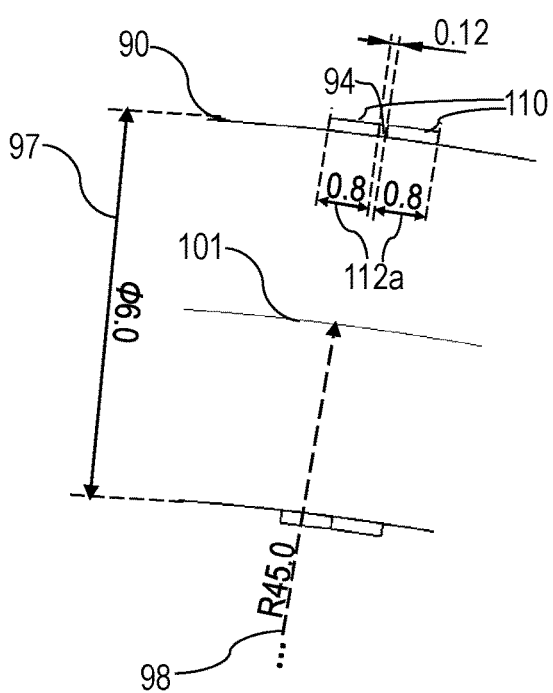
Figure 2E:
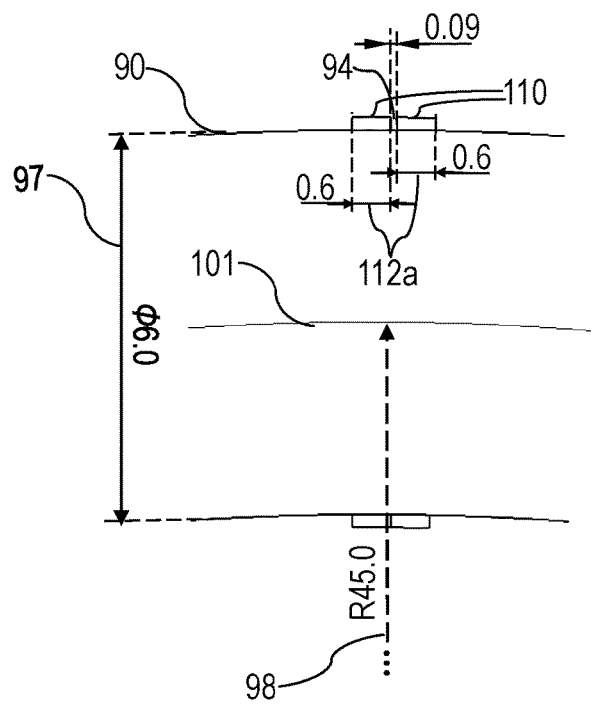
Figure 2F:
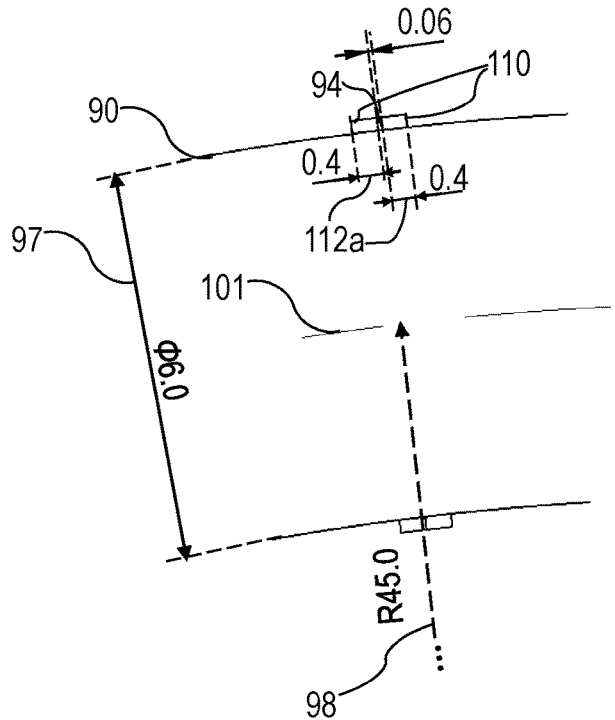

Upon bending of elongated device 90 supported within device 100, gaps 94 may be formed between adjacent members 110 on a convex side 91 of bended elongated element 90, while on a concave side 92 thereof members 110 may remain adjacent (or substantially adjacent) with respect to each other (e.g., as shown in FIG. 1E). For example, gaps 96 on concave side 92 may be smaller than gaps 94 on convex side 91 of elongated element 90 by at least one order of magnitude.

According to some embodiments, members 110 are shaped to ensure that gaps 94 between adjacent members 110 formed on convex side 91 of bended elongated element 90 do not exceed a predetermined gap threshold value.

In some embodiments, members 110/peripheral portions 112 of members 110 are made of a metal wire (e.g., stainless steel or titanium) having a rectangular (or substantially rectangular) cross-section (e.g., as shown in FIGS. 1C, 1D and 1E). The rectangular cross-section of peripheral portions 112 of members 110 may have a first dimension 112a (e.g., in a direction along, or substantially along, longitudinal axis 101 of device 100) and a second dimension 112b that is perpendicular to first dimension 112a (e.g., as shown in FIG. 1E).

In some embodiments, first dimension 112a of the cross-section of peripheral portion 112 of members 110 ranges between 0.1-3.0 mm. In some embodiments, second dimension 112b of the cross-section of peripheral portion 112 of members 110 ranges between 0.05-0.3 mm.

In some embodiments, the predetermined gap threshold value is no more than 0.05 mm. In some embodiments, the predetermined gap threshold value is no more than 0.5 mm.

When the bending of elongated element 90 is complete, device 100 may be released (e.g., slidably removed) from elongated element 90.

Reference is now made to FIGS. 2A, 2B, 2C, 2D, 2E and 2F, which are schematic illustrations of various configurations of members 110 of a device 100 for maintaining a shape of a transverse cross-sectional profile of an elongated element 90, according to some embodiments of the invention.

According to some embodiments, the smaller first dimension 112a of peripheral member portions 112 of members 110, the smaller gaps 94 formed between adjacent members 110 on convex side 91 of elongated element 90 upon bending thereof.

For example, FIGS. 2A-2F show a rod as an example of elongated element 90, the rod having a diameter 97 of 6 mm, supported within device 100 and being bent to provide a curvature radius 98 of 45 mm in the bending region.

It is noted that such a small curvature radius 98 (e.g., of 45 mm) may be required in extreme cases during, for example, orthopedic surgeries. Such cases may, for example, include adjusting elongated element 90 (e.g., the rod) of, for example, a pedicle screw assembly to fit curvature of a spinal cord between L5-S1 spinal segments thereof.

FIGS. 2A, 2B, 2C, 2D, 2E and 2F further show an example of various configurations of device 100 in which members 110 have peripheral member portions 112 with, for example, first dimension 112a of 2.0, 1.4, 1.0, 0.8, 0.6 and 0.4 mm, respectively, that provide gaps 94 on convex side 91 of elongated element 90 (upon bending thereof) of 0.31, 0.21, 0.15, 0.12, 0.09 and 0.06 mm, respectively. It is noted that FIGS. 2A-2F show portions of elongated element 90 and of two adjacent members of multiple members 110 only for sake of clarity.

In some embodiments, second dimension 112b of peripheral member portions 112 of members 110 has no effect (or substantially has no effect) on gaps 94 formed between adjacent members 110 on convex side 91 of bended elongated element.

In some embodiments, second dimension 112b is determined to prevent overlapping of adjacent members 110 onto each other on concave side 92 of bended elongated element 90. In some embodiments, second dimension 112b of peripheral member portions 112 of members 110 ranges between 0.05-0.3 mm.

Figure 3A:
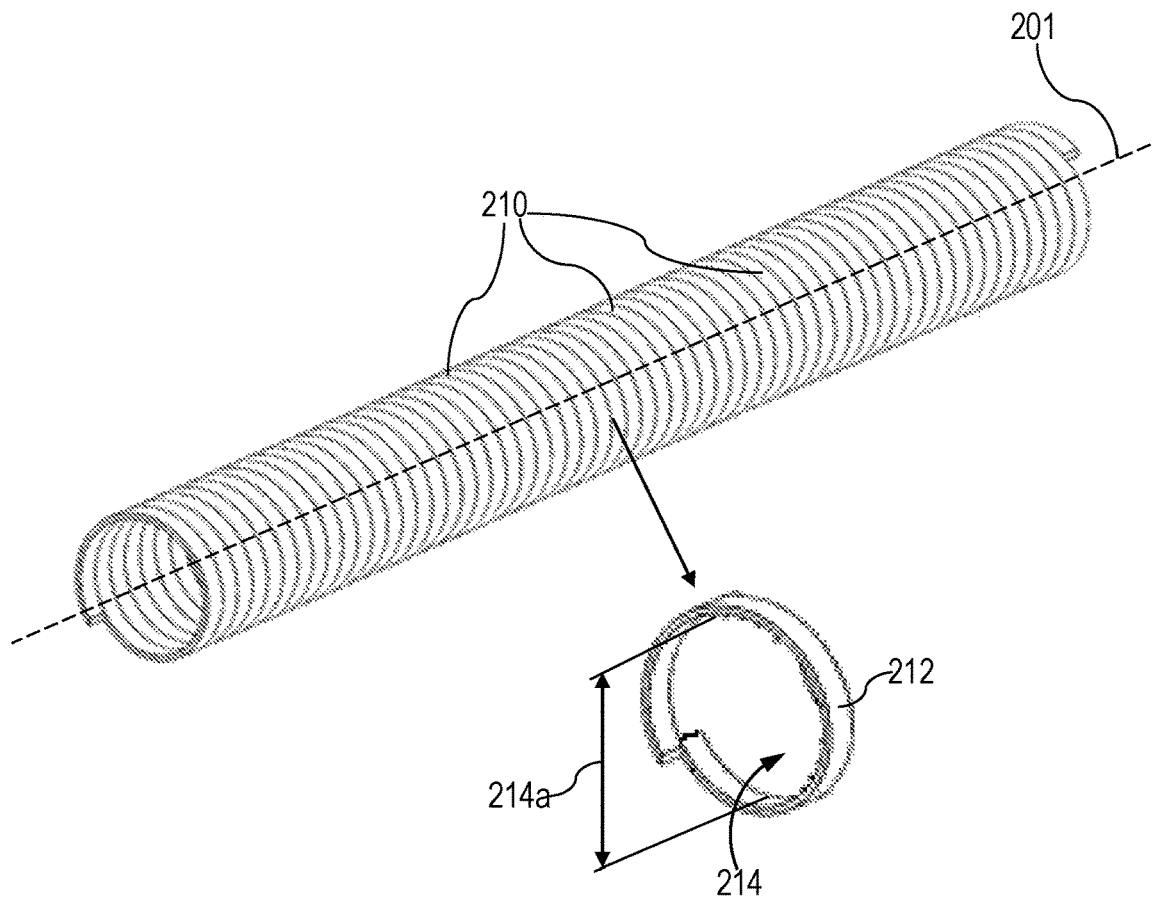
FIGS. 3A and 3B are schematic illustrations of a coiled device for maintaining a shape of a transverse cross-sectional profile of an elongated element, according to some embodiments of the invention.
Figure 3B:
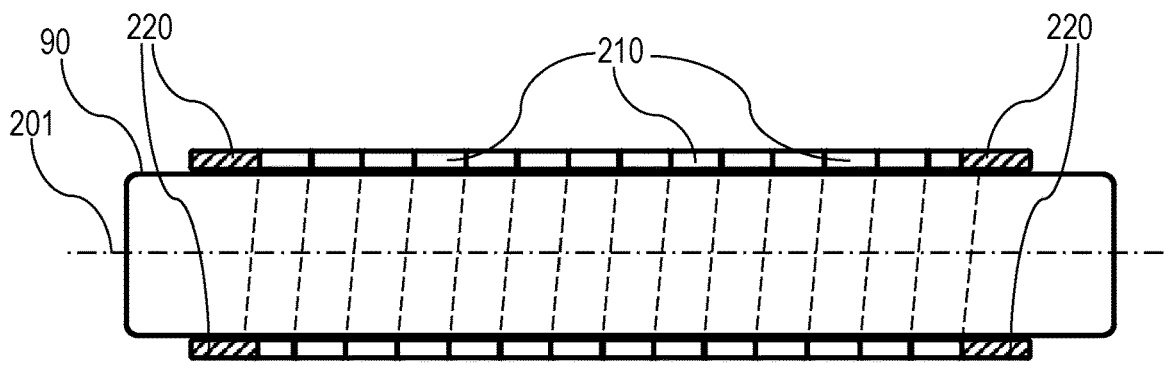

Reference is now made to FIGS. 3A and 3B, which are schematic illustrations of a coiled device 200 for maintaining a shape of a transverse cross-sectional profile of an elongated element 90, according to some embodiments of the invention.

According to some embodiments, coiled device 200 includes multiple coils 210 arranged along a longitudinal axis 201 of device 200, wherein adjacent coils of multiple coils 210 are helically connected with each other to form coiled device 200 (e.g., as shown in FIG. 3A).

In some embodiments, coils 210 of device 200 may be similar to members 110 of device 100 described above with respect to FIGS. 1A-1E and FIGS. 2A-2F. In some embodiments, coiled device 200 may be made by helically connecting adjacent members of multiple members 110 of device 100 (e.g., described above with respect to FIGS. 1A-1E and FIGS. 2A-2F) with each other.

Coiled device 200 may enable a desired measure of relative motion of coils 210 (e.g., of coils of device 200) with respect to each other. Coiled device 200 may enable a desired measure of deformation and/or elasticity of peripheral member portions 212 of coils 210 in a direction that is perpendicular to longitudinal axis 201 of device 200. For example, coils 210/peripheral portions 212 of coils 210 may slightly expand/collapse in the direction that is perpendicular to longitudinal axis 201.

In some embodiments, dimensions 214a of central member opening 214 of coils 210 of coiled device 200 are slightly smaller (by no more than 5%) as compared to dimensions of the cross-sectional profile of elongated element 90 to be used with.

For example, if elongated element 90 is a rod having a diameter of 6 mm, then inner diameter 214a of central member opening 214 of coils 210 may be, for example 5.9 mm Thus, coils 210 may slightly expand when receiving rod 90 and further push onto rod 90 upon receiving of rod 90 therein, thereby providing tight support of rod 90 within coiled device 200.

In some embodiments, stoppers 220 removably affix coils 210 at both ends of coiled device 200 (e.g., as shown in FIG. 3B) to, for example, prevent undesired twisting/untwisting and/or axial sliding of coiled device 200 during bending. Stoppers 220 may be similar to stoppers 120 described above with respect to FIGS. 1C and 1D.

Figure 3C:
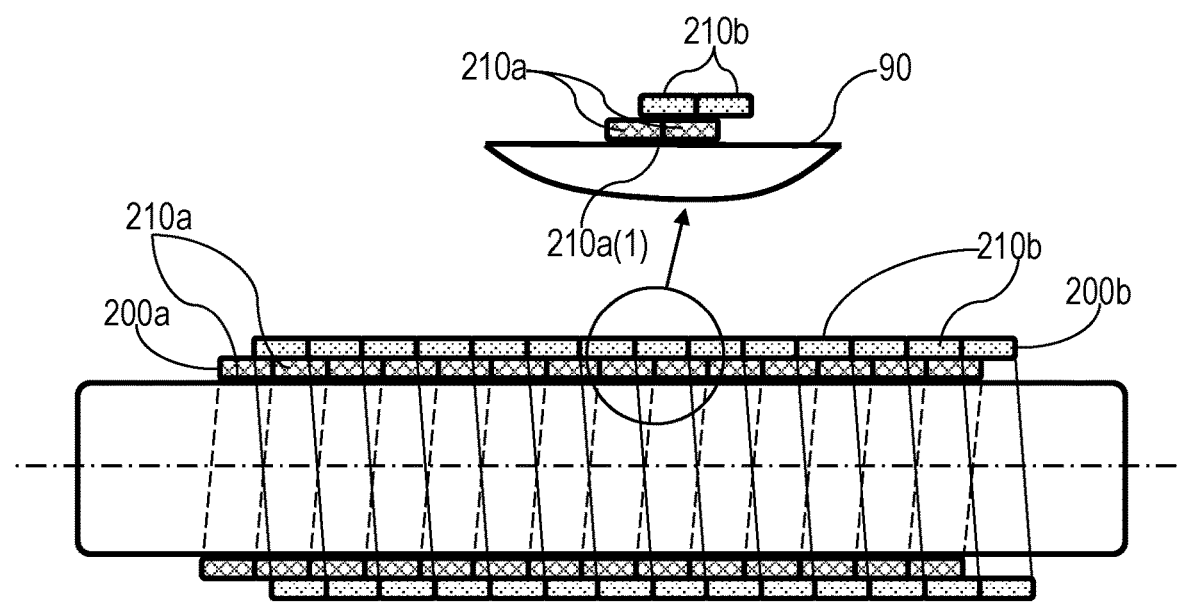
FIGS. 3C and 3D are schematic illustrations of an assembly including two coiled devices for maintaining a shape of a transverse cross-sectional profile of an elongated element, according to some embodiments of the invention.
Figure 3D:
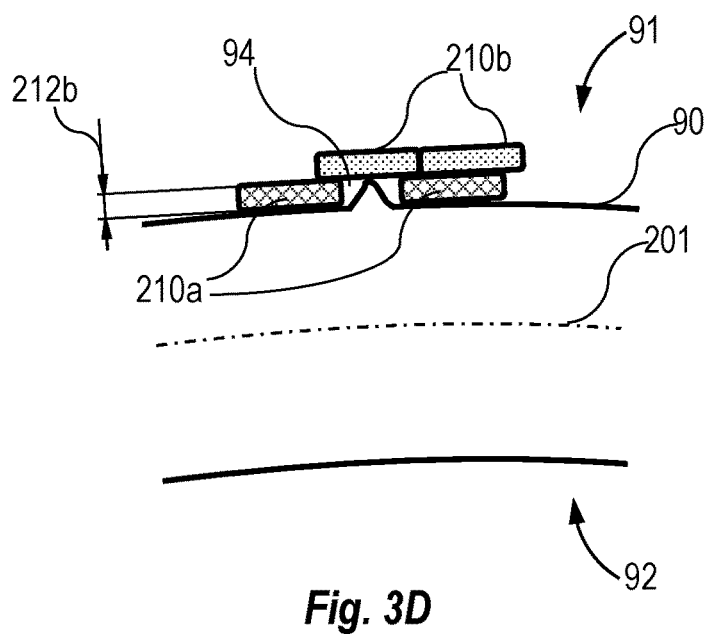

Reference is now made to FIGS. 3C and 3D, which are schematic illustrations of an assembly 202 including two coiled devices 200a, 200b for maintaining a shape of a transverse cross-sectional profile of an elongated element 90, according to some embodiments of the invention.

According to some embodiments, more than one coiled device 200 may be used with elongated element 90. For example, a first coiled device 200a having first coils 210a and a second coiled device 200b having second coils 210b may be used (e.g., coiled devices 200a and 200b as shown in FIG. 3C).

First coiled device 200a may tightly receive and support elongated element 90 (e.g., as described above with respect to 3A-3B). Second coiled device 200b may tightly receive and support first coiled device 200a with elongated element 90 supported therein (e.g., as shown in FIG. 3C).

In some embodiments, second coiled device 200b is positioned with respect to first coiled device 200a such that second coils 210b of second coiled device 200b overlap with regions of contact 210a (1) between adjacent first coils 210a of first coiled device 200a (e.g., as shown in FIGS. 3C and 3D).

Such relative positioning of second coiled device 200b with respect to first coiled device 200a may, for example, limit a measure of protrusion of portions of heated elongated element 90 into gaps 94 between adjacent first coils 210a of first coiled device 200a when heated elongated element 90 is being bent. In this manner, portions of heated elongated element 90 may not protrude into gaps 94 more than second dimension 212b of peripheral member portions 212 of first coils 210a (e.g., as shown in FIG. 3D).

Figure 4A:
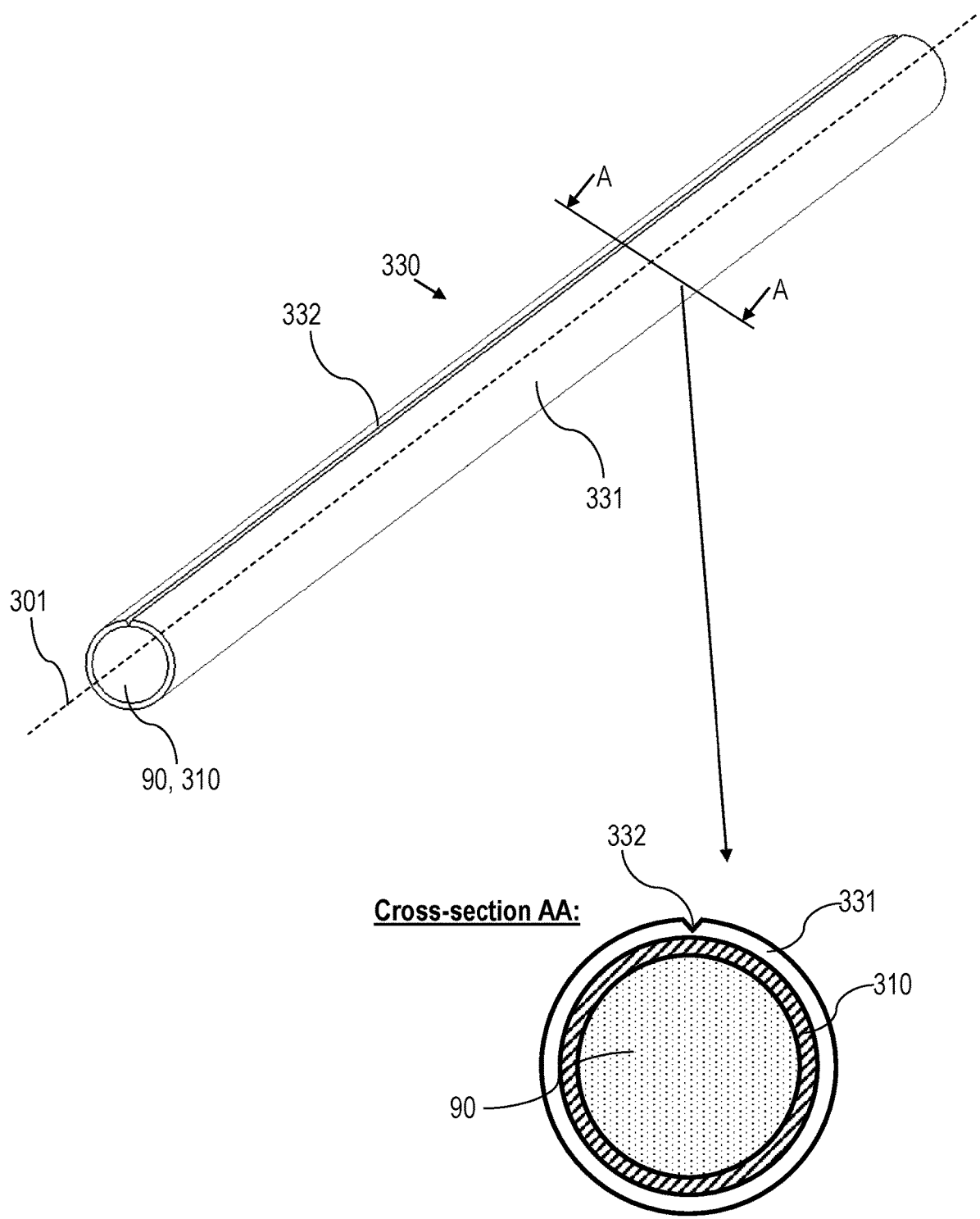
FIGS. 4A, 4B and 4C are schematic illustrations of an assembly including a device for maintaining a shape of a transverse cross-sectional profile of an elongated element and an envelope, according to some embodiments of the invention.
Figure 4B:
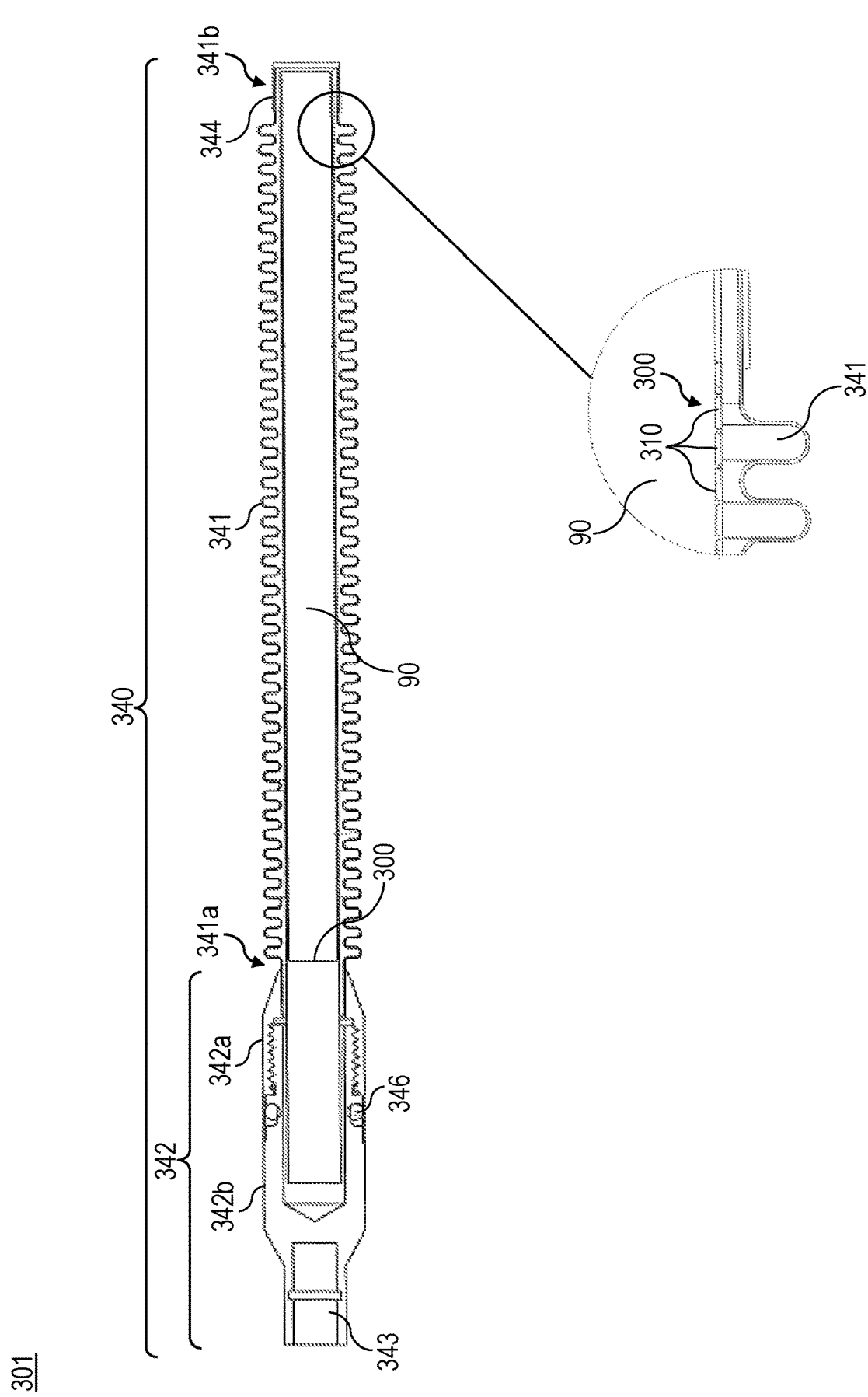
Figure 4C:
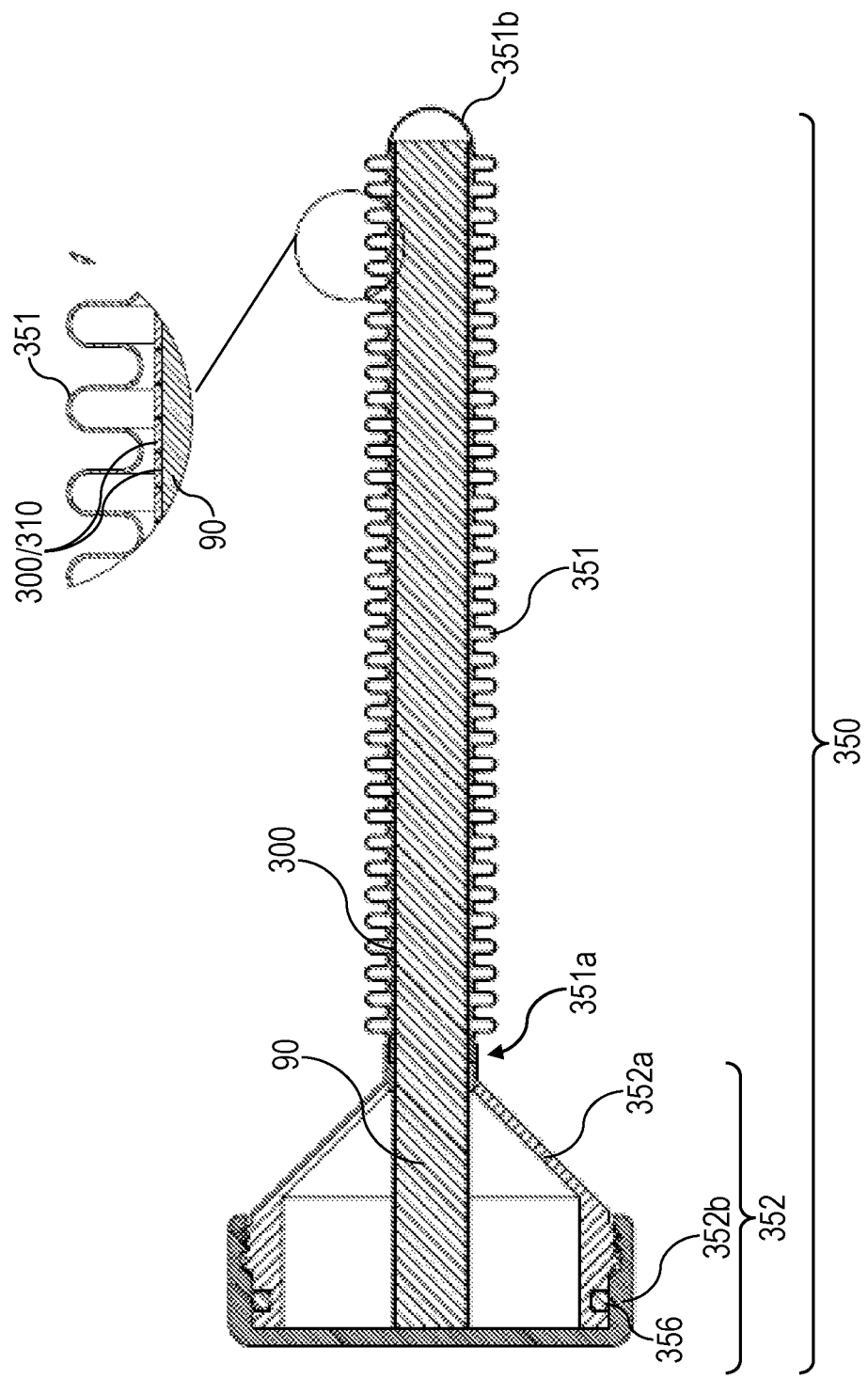

Reference is now made to FIGS. 4A, 4B and 4C, which are schematic illustrations of an assembly 301 including a device 300 for maintaining a shape of a transverse cross-sectional profile of an elongated element 90 and an envelope 330, 340, and 350, respectively, according to some embodiments of the invention.

FIG. 4A shows an isometric view of assembly 301 and a cross section AA of assembly 301. FIGS. 4B and 4C show longitudinal cross-section views of assembly 301.

According to some embodiments, assembly 301 includes a device 310 for maintaining a shape of a cross-sectional profile of an elongated element 90 and an envelope. FIGS. 4A, 4B and 4C show schematic illustrations of a first embodiment of an envelope 330, a second embodiment of an envelope 340 and a third embodiment of an envelope 350, respectively.

Device 300 may include multiple members 310 arranged along a longitudinal axis 301 of device 300. In various embodiments, device 300 and members 310 may be similar to device 100 and members 110, respectively, described above with respect to FIGS. 1A-1E and FIGS. 2A-2F and/or to device 200 and coils 210, respectively, described above with respect to FIGS. 3A-3B.

The envelope may surround members 310 and elongated element 90 supported therein. The envelope may be made of an elastic material. The envelope may be made of a material that does not undergo thermal deformation at the predetermined temperature value (e.g., at 400° C.). The envelope may be made of a biocompatible material. The envelope may be arranged to be released from members 310/elongated element 90 after bending of elongated element 90.

FIG. 4A schematically shows a first embodiment of an envelope 330. Envelope 330 may include a tube 331. Tube 331 may be made of, for example, nitinol. Tube 331 may be adapted in shape and dimensions to tightly envelope members 310 of device 300. Tube 331 may include an indent 332 along the entire (or substantially the entire) length of tube 331. The strength of tube 331 in vicinity of indent 332 may be smaller as compared to other regions of tube 331. The measure of indentation of indent 332 into walls of tube 331 may be predetermined to enable breaking or tearing and releasing of tube 331, for example, after bending of elongated element 90 and before implanting elongated element 90 into a patient's body.

FIG. 4B schematically shows a second embodiment of an envelope 340. Envelope 340 may include a bellow tube 341. The use of a bellow tube, such as bellow tube 341, may provide an air-tight cover which is flexible enough to enable bending it with its content. It will be apparent that other envelopes providing these features may be used for this purpose. Bellow tube 341 portion of envelope 340 may cover at least part of elongated element 90 when it is inserted to a rest place within bellow tube 341. Envelope 340 may be made of, for example, stainless steel. Envelope 340 may, for example, include a first cap 342 adapted to close a first end 341a of bellow tube 341 and a second cap 344 adapted to close a second end 341b of bellow tube 341.

In some embodiments, first cap 342 may include a proximal first-cap part 342a and a distal first-cap part 342b. Proximal first-cap part 342a may be connected to first end 341a of bellow tube 341, and distal first-cap part 342b may be screwable onto proximal first-cap part 342a. In some embodiments, envelope 340 may include a seal 346. Seal 346 may be disposed between proximal first-cap part 342a and distal first-cap part 342b.

In some embodiments, first cap 342, for example, distal first-cap part 342b, may include a connector 343 for a rod used to insert assembly 301 into a heating device for heating.

When distal first-cap part 342b is unscrewed from proximal first-cap part 342a, an end of elongated element 90 may protrude from proximal first-cap part 342a and may be slidably released from envelope 340.

FIG. 4C schematically shows a third embodiment of an envelope 350. Envelope 350 may include a bellow tube 351. Envelope 350 may be made of, for example, stainless steel. Envelope 350 may, for example, include a cap 352 adapted to close a first end 351a of bellow tube 351. Bellow tube 351 portion of envelope 350 may cover at least part of elongated element 90 when it is inserted to a rest place within bellow tube 351. Second end of 351b of bellow tube 351 may be, for example, a closed end.

In some embodiments, cap 352 may include a first cap part 352a and a second cap part 352b. First cap part 352a may be connected to first end 351a of bellow tube 351, and second cap part 352b may be screwable onto first cap part 352a. In some embodiments, envelope 350 may include a seal 356. Seal 356 may be disposed between first cap part 352a and second cap part 352b.

When second cap part 352b is unscrewed from first cap part 352a, elongated element 90 may be slidably released from envelope 350.

In some embodiments, assembly 301 may be provided as a kit further including elongated element 90. Elongated element 90, device 300 and at least an inner portion of the envelope may be sterile. An outer portion of the envelope may be not sterile. Device 310 may be thread onto elongated element 90, and both may be inserted into the envelope. The envelope accommodating sterile elongated element 90 and sterile device 310 may be inserted into a heating device for heating of elongated element 90 and then inserted into a bending device for bending elongated element 90 while keeping elongated element 90 and device 310 sterile. Upon bending and cooling, a person having a non-sterile hand may hold the envelope and, for example, unscrew the cap thereof (e.g., as described above with respect to FIGS. 4B and 4C), while a person having a sterile hand may remove sterile elongated element 90 from within the envelope. In this manner, the envelope may enable using non-sterile heating device and/or non-sterile bending device.

As described above, elongated element 90 containing thermoplastic polymer(s) should be heated or pre-heated in order to be shaped (e.g., bent). In some embodiments, heating/pre-heating of elongated element 90 is done using any heating means known in the art. For example, elongated element 90 may be heated using laser, infrared radiation, or induction or resistant prior to positioning of elongated element 90 into a bending device or upon positioning of elongated element 90 in the bending device.

In some embodiments, elongated element 90 may be disposed within a cross-sectional profile maintaining device prior to heating and bending thereof (e.g., device 100, 200, as described above with respect to FIGS. 1A-1E and 2A-2F, FIGS. 3A-3B, respectively). In some embodiments, elongated element 90 with the cross-sectional profile maintaining device may be disposed within an envelope prior to heating and bending thereof (e.g., envelope 330, 340, 350 described above with respect to FIGS. 4A, 4B, 3C, respectively).

For sake of clarity, the description below made with respect to FIGS. 5, 6A-6C, 7A-7E, 8A-8E, 9A-9B, and 10A-10C refers to a "elongated assembly" or "elongated assembly 80", wherein elongated assembly 80 may include at least one of: elongated element 90, elongated element 90 removably disposed within the cross-sectional profile maintaining device and the envelope removably accommodating elongated element 90 disposed within the cross-sectional profile maintaining device.

Figure 5:
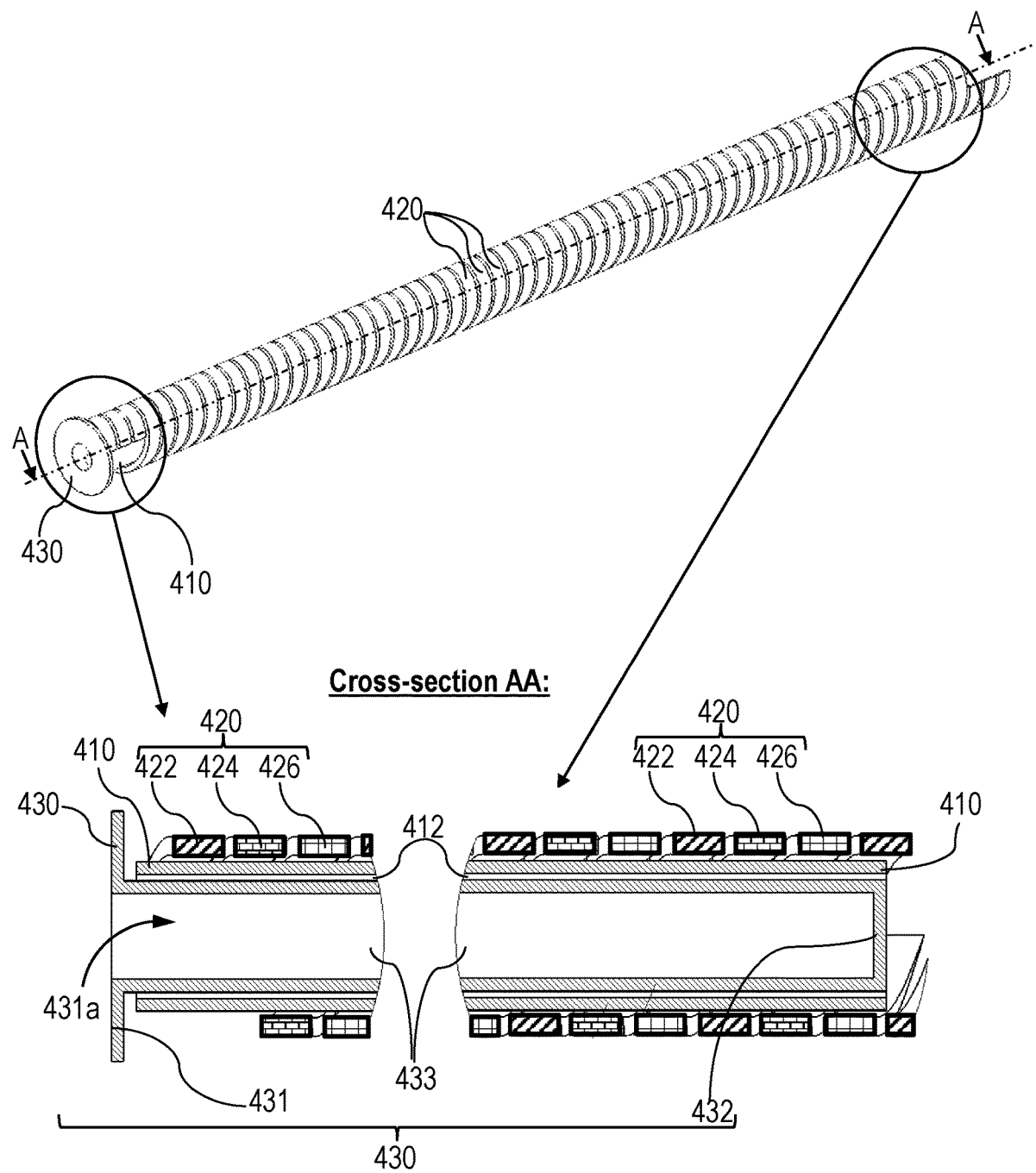
FIG. 5 is a schematic illustration of a heating device for heating an elongated assembly, according to some embodiments of the invention.

Reference is now made to FIG. 5, which is a schematic illustration of a heating device 400 for heating an elongated assembly, according to some embodiments of the invention.

According to some embodiments, heating device 400 includes a housing 410 and at least one heating element 420 that at least partly envelopes housing 410.

In some embodiments, housing 410 is an annular (or substantially annular) body (e.g., as shown in FIG. 5). Housing 410 may have an interior 412 that is arranged to receive and accommodate the elongated assembly. It is noted that the elongated assembly is not shown in FIG. 5 for sake of clarity.

In some embodiments, at least one heating element 420 has a helical shape and envelopes housing 410 along the entire (or substantially entire) length of housing 410. For example, heating device 400 may include three heating elements: a first heating element 422, a second heating element 444 and a third heating element 426 (e.g., as shown in FIG. 5). Use of more than one heating element may enable heating of the elongated assembly, even when one of heating elements fails.

In some embodiments, heating element(s) 420 may be low voltage, optionally battery-operated. For example, heating element(s) 420 be operated by 48 Volt DC battery.

According to some embodiments, heating device 400 is sterile. For example, heating device 400 may be made of materials that enable sterilization of the entire heating device (e.g., including housing and heating element set 420) before/after each operational procedure.

According to some embodiments, heating device 400 may not require sterilization.

In some embodiments, the elongated assembly may include the envelope accommodating elongated element disposed within the cross-sectional profile maintaining device, wherein the envelope may keep elongated element 90 sterile during heating and/or bending thereof (e.g., as described above with respect to FIGS. 4A-4C).

In some embodiments, heating device 400 includes a heating envelope 430 (e.g., as shown in FIG. 5). Heating envelope 430 may be made of a material that may be sterilized (e.g., stainless steel).

Heating envelope 430 may include a first heating envelope end 431, a second heating envelope end 432 and a heating element interior 433. Heating envelope 430 may include an opening 431a on, for example, first heating envelope end 431 and may, for example, be closed at second heating envelope end 432.

Heating envelope 430 may receive, through opening 431a, and may accommodate within heating envelope interior 433, the elongated assembly. Heating envelope 430 with the elongated assembly may be positioned within a housing interior 412 of housing 410. Heating device 400 may be adapted to supply a desired measure of heat energy though heating element(s) 420 to elevate the temperature of the elongated assembly and particularly of elongated element 90 disposed therein up to the predetermined temperature value (e.g., 400° C.).

In this manner (e.g., using envelope 330, 340, 350 or heating envelope 430), the elongated assembly and particularly elongated element 90 disposed therein may be heated to the predetermined temperature value while eliminating a need in sterilizing heating device 400 before/after each operational procedure.

According to various embodiments, the elongated assembly and heating envelope 430 are part of a kit.

Figure 6A:
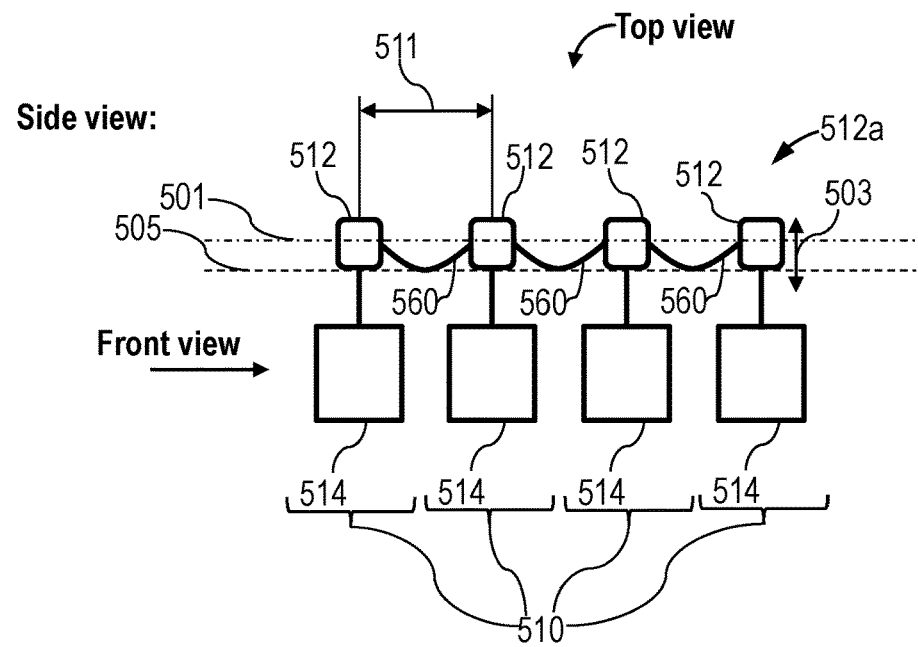
FIGS. 6A, 6B and 6C are schematic illustrations of a bending device for bending an elongated assembly, according to some embodiments of the invention.
Figure 6A:
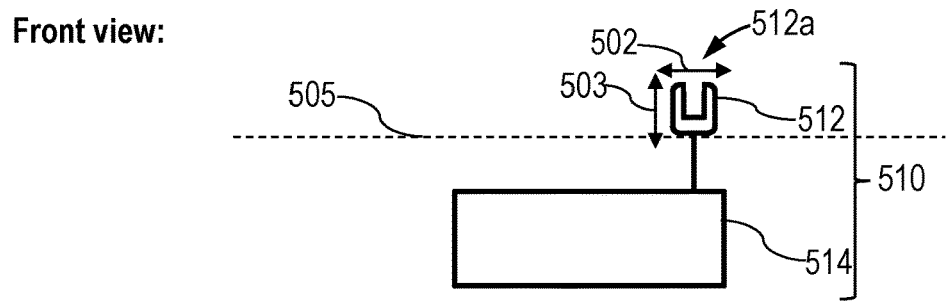
Figure 6A:
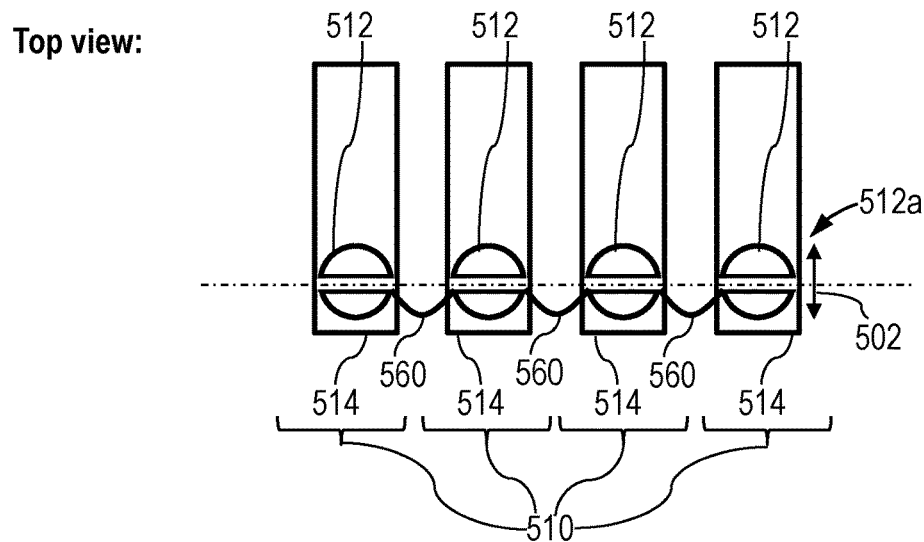
Figure 6B:
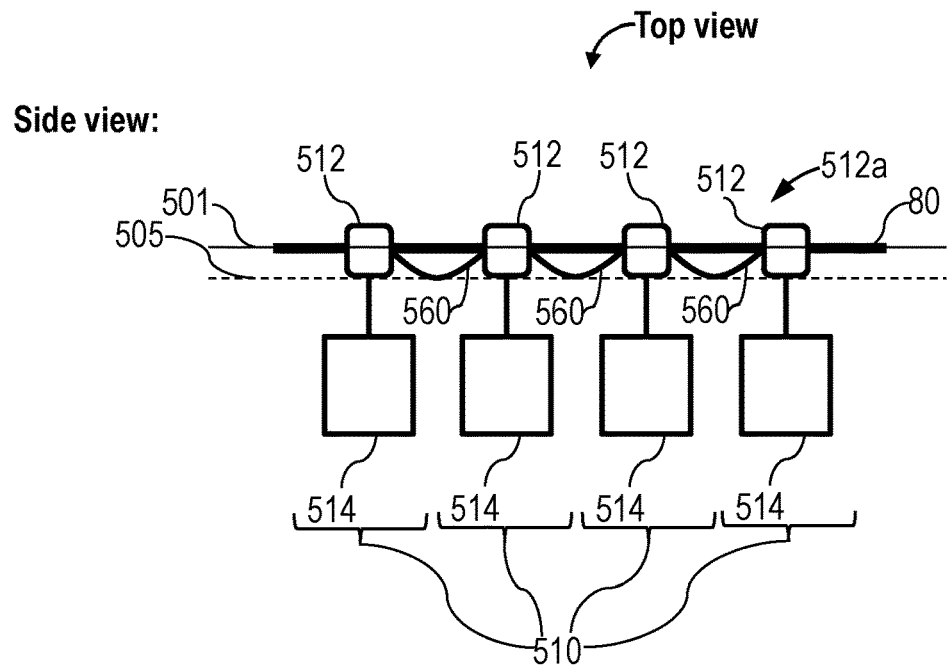
Figure 6B:
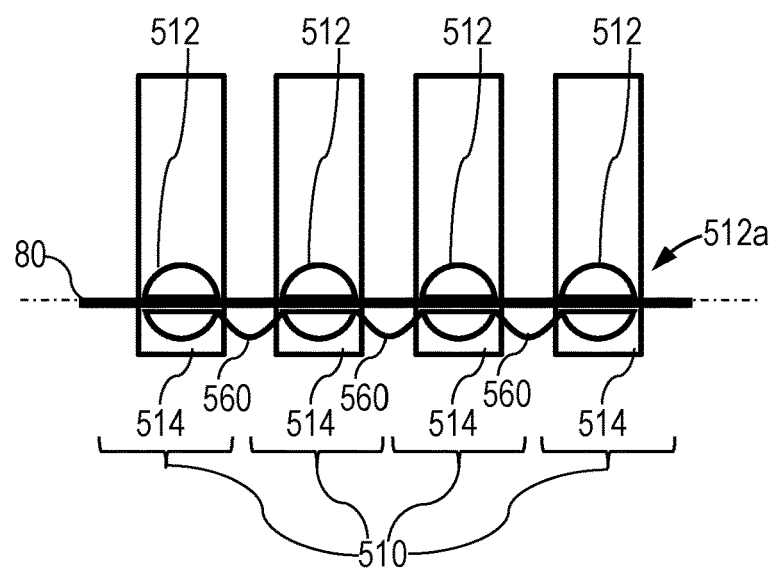
Figure 6C:
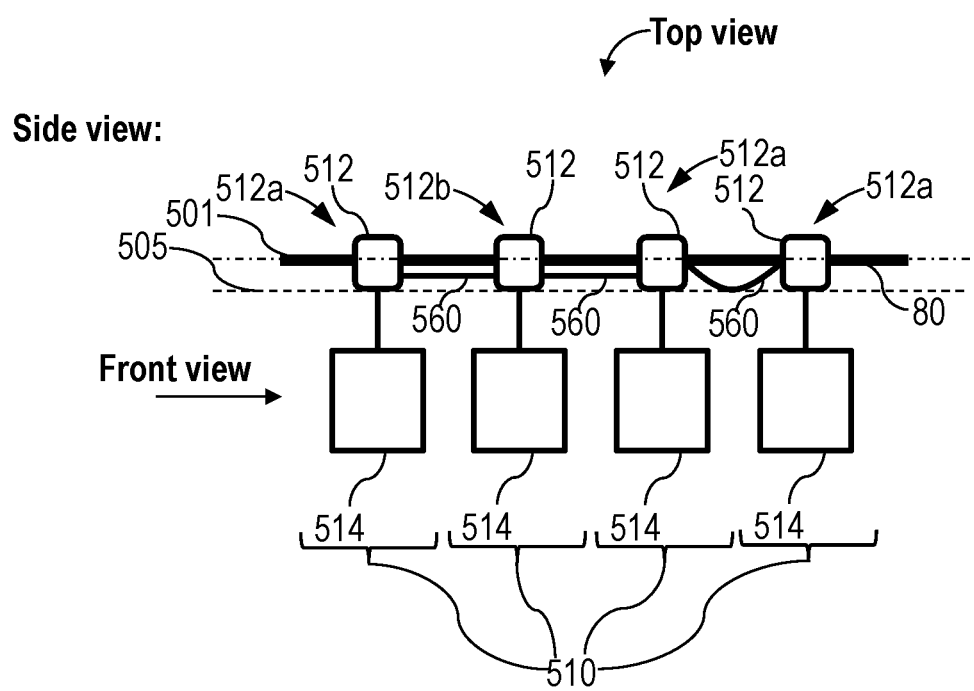
Figure 6C:
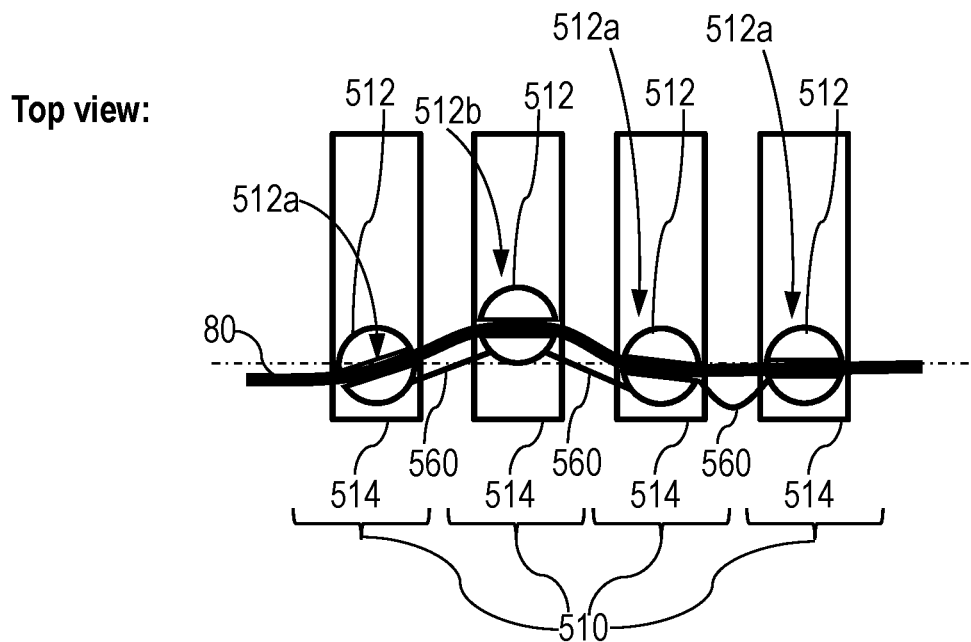

Reference is now made to FIGS. 6A, 6B and 6C, which are schematic illustrations of a bending device 500 for bending an elongated assembly 80, according to some embodiments of the invention.

According to some embodiments, bending device 500 includes multiple bending units 510 (e.g., as shown in FIG. 6A). Bending units 510 may be positioned at a distance 511 with respect to each other (e.g., as shown in FIG. 6A). In some embodiments, distance 511 between adjacent bending units 510 ranges between 10-20 mm. In some embodiments, a number of bending units 510 ranges between 10-30. It is noted that FIGS. 6A, 6B and 6C show four (4) bending units 510 for sake of clarity.

Each of bending units 510 may include a receiving member 512 and a driving assembly 514 (e.g., as shown in FIG. 6A).

Each of receiving members 512 of bending units 510 may be movable between an initial position 512a (e.g., as shown in FIGS. 6A and 6B) and at least one other position 512b (e.g., as shown in FIG. 6C).

Receiving members 512 may be aligned along a longitudinal axis 501 of bending device 500 in a plane 505 when all receiving members 512 are in their initial positions 512a (e.g., as shown in FIGS. 6A and 6B). Receiving members 512 of bending units 510 may be arranged to receive, when in initial position 512a, corresponding portions of elongated assembly 80 (e.g., as shown in FIG. 6B). It is noted that elongated assembly 80 is not shown in FIG. 6A for sake of clarity only.

Each of receiving members 512 may be movable in a first direction 502 and/or in a second direction 503 that is perpendicular to longitudinal axis 501 when moved between its respective initial position 512a and at least one other position 512b (e.g., as shown in FIG. 6A). For example, driving assemblies 514 of bending units 510 may be arranged to move respective receiving members 512 between their respective initial and at least one other positions 512a, 512b, respectively.

The direction of movement and/or the measure of movement and/or at least one other position 512b of each of receiving members 512 may be determined based on, for example, a desired bending profile of elongated element 90 disposed within elongated assembly 80. The desired bending profile of elongated element 90 may be determined/predetermined based on, for example, an anatomy of an implantation site of elongated element 90 (e.g., as described below with respect to FIG. 11).

Elongated assembly 80 may be pre-heated (e.g., using heating device 400 as described above with respect to FIG.

5) prior to positioning thereof in bending device 500. Alternatively, elongated assembly 80 may be heated upon positioning thereof in bending device 500 using, for example, laser or infrared radiation.

Upon positioning of elongated assembly 80 in bending device 500, receiving member 512 of at least one of bending units 510 may be moved from its initial position 512*a* to one of its other positions 512*b* in one or two directions 502, 503, based on the predetermined bending profile, thereby bending elongated assembly 80 and elongated element 90 disposed therein into a desired shape. For example, FIG. 6C shows receiving member 512 of one of bending units 510 in one of its other positions 512*b* and receiving members 512 of other bending units 510 in their initial position 512*a*.

In some embodiments, receiving members 512 of bending units 510 may rotate (e.g., about an axis perpendicular to plane 505) to provide smooth bending of elongated assembly 80 and elongated element 90 disposed therein (e.g., as shown in FIG. 6C).

In this manner, elongated element 90 (e.g., disposed within elongated assembly 80) containing thermoplastic polymer(s) may be bent according to the predetermined bending profile while preventing distortion of the shape of the cross-sectional profile of elongated element 90 in the bending regions thereof.

According to some embodiments, bending device 500 includes connectors 560. Connectors 560 may be, for example, deformable wires or ropes. Each of connectors 560 may be connected at its end to receiving members 512 of adjacent bending units 510 (e.g., as shown in FIGS. 6A-6C). Connectors 560 may limit the measure of movement of adjacent receiving members 512 with respect to each other, thereby limiting a bending radius of elongated element 90 in the bending region thereof. The length of connectors 560 may be determined to ensure that the bending radius of elongated element 90 in the bending region will not exceed a predetermined bending radius value. In some embodiments, the predetermined bending radius value is 45 mm.

Reference is now made to FIGS. 7A, 7B, 7C, 7D and 7E, which are schematic illustrations of a bending device 600 for bending an elongated assembly, including bending units 610 with mechanically adjustable driving assemblies 614, according to some embodiments of the invention.

Figure 7A:
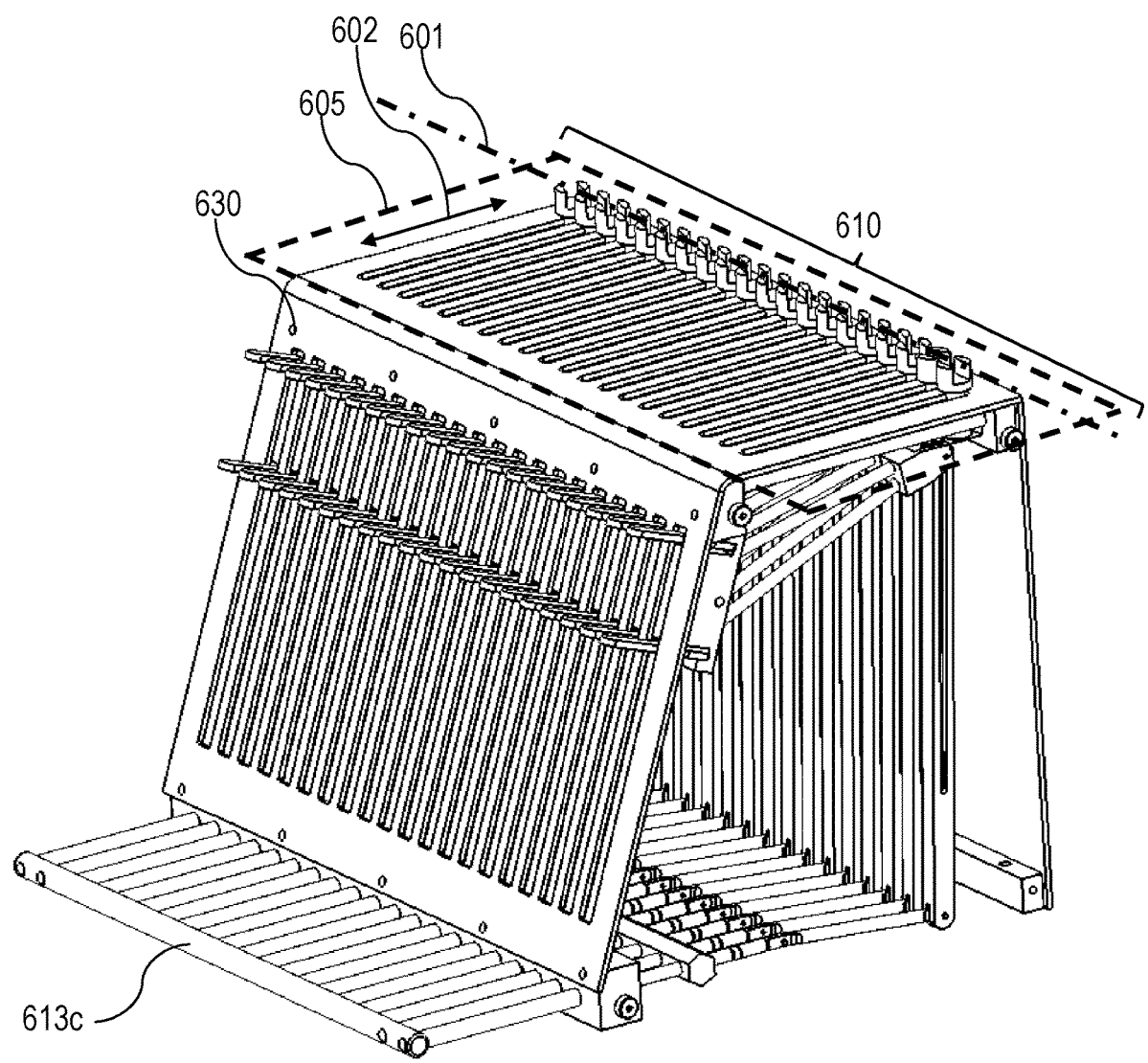
FIGS. 7A, 7B, 7C, 7D and 7E are schematic illustrations of a bending device for bending an elongated assembly and including bending units with mechanically adjustable driving assemblies, according to some embodiments of the invention.
Figure 7B:
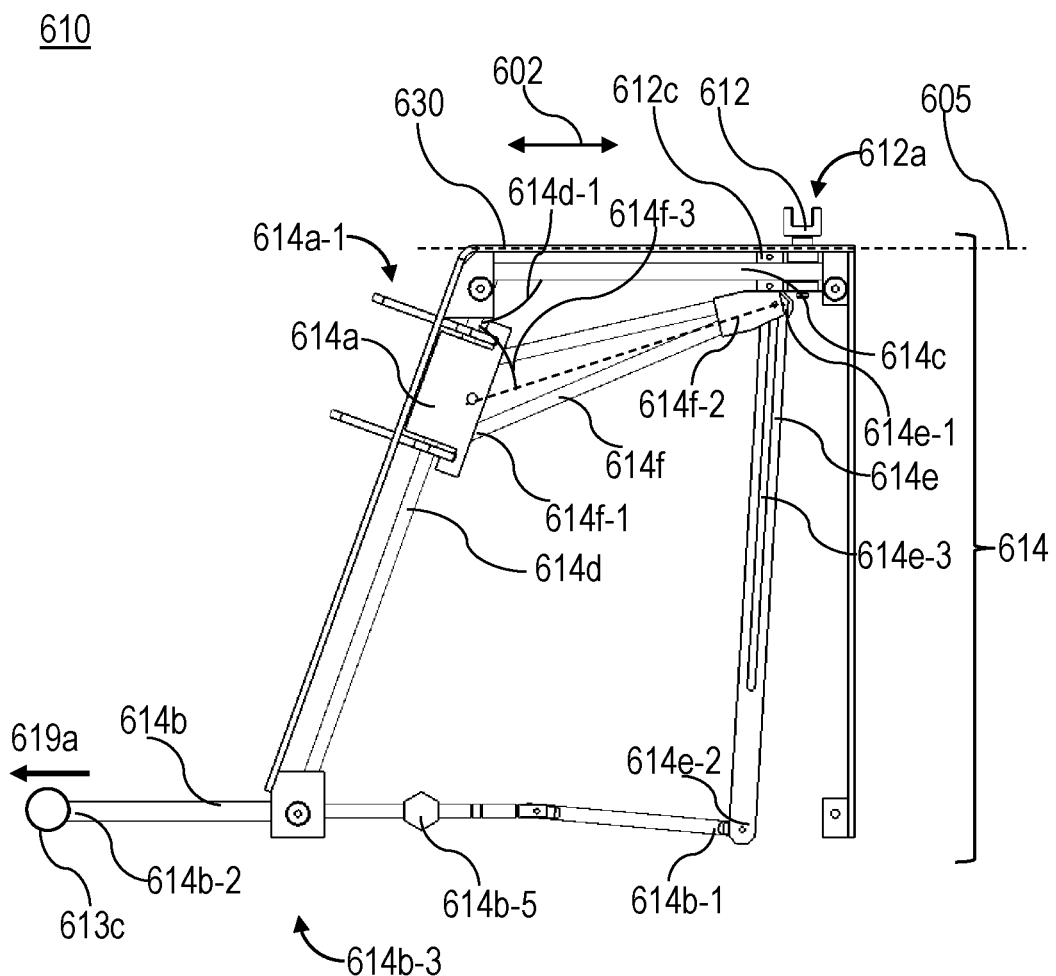

FIG. 7A shows a perspective view of bending device 600, and FIGS. 7B, 7C, 7D and 7E show a side view of a single bending unit 610.

According to some embodiments, bending device 600 includes a housing 630 arranged to accommodate multiple bending units 610 of bending device 600 (e.g., as shown in FIG. 7A).

According to some embodiments, each of bending units 610 includes receiving member 612 and driving assembly 614 coupled to a respective receiving member 612 and arranged to move respective receiving member 612 based on the predetermined bending profile of elongated element 90.

In some embodiments, bending units 610 (e.g., receiving members 612 and driving assemblies 614) of device 600 may be similar to bending units 510 (e.g., receiving members 512 and driving assemblies 514) as described above with respect to FIGS. 6A-6C.

FIGS. 7B, 7C, 7D and 7E show single bending unit 610 for sake of clarity. It is noted that other bending units 610 may have similar structure and operate in similar way.

According to some embodiments, driving assembly 614 of each of bending units 610 includes a mover 614*a* and an actuation arm 614*b*.

Mover 614*a* of each of bending units 610 may be movable between an initial mover position 614*a*-1 and at least one another mover position 614*a*-2 and arranged to define/dictate the measure movement of respective receiving member 612, upon actuation by respective actuation arm 614*b* (e.g., as described below with respect to FIGS. 7B, 7C, 7D and 7E).

According to some embodiments, each of driving assemblies 614 of each of bending units 610 includes a first rail 614*c*, a second rail 614*d*, a rotatable arm 614*e* and a rotational axis arm 614*f* (e.g., as shown in FIGS. 7B, 7C, 7D and 7E).

According to some embodiments, first rail 614*c* of each of driving assemblies 614 may be coupled at its ends to housing 630 in a plane that is parallel to plane 605 and in first direction 602 (e.g., as shown in FIGS. 7B, 7C, 7D and 7E).

According to some embodiments, receiving member 612 of each of bending units 610 may be coupled at its end 612*c* to respective first rail 614*c* and arranged to move along respective first rail 614*c* between its respective initial position 612*a* and at least one other position 612*b*.

According to some embodiments, rotatable arm 614*e* of each of driving assemblies 614 may be pivotally coupled at its first end 614*e*-1 to an end 612*c* of respective receiving member 612 and may be pivotally coupled at its second end 614*e*-2 to a first end 614*b*-1 of respective actuation arm 614*b*.

According to some embodiments, a second end 614*b*-2 of actuation arm 614*b* of each of driving assemblies 614 may extend from housing 630. In some embodiments, second ends 614*b*-2 of actuation arms 614*b* of driving assemblies 614 of all bending units 610 are connected using an actuation rod 613*c*.

Actuation arm 614*b* of each of driving assemblies 614 may be movable (e.g., in a plane parallel to plane 605 and in first direction 602) between its initial position 614*b*-3 and extended position 614*b*-4.

In some embodiments, actuation arm 614*b* of each of driving assemblies 614 includes one or more stoppers 614*b*-5 to restrict motion of actuation arm 614*b* between its initial position 614*b*-3 and extended position 614*b*-4.

In some embodiments, actuation arms 614*b* of all driving assemblies 614 of all bending units 610 may be simultaneously moved, for example, by manually pushing/pulling actuation rod 613*c* (with respect to housing 630) that connects second ends 614*b*-2 of actuation arms 614*b* of driving assemblies 614.

Figure 7C:
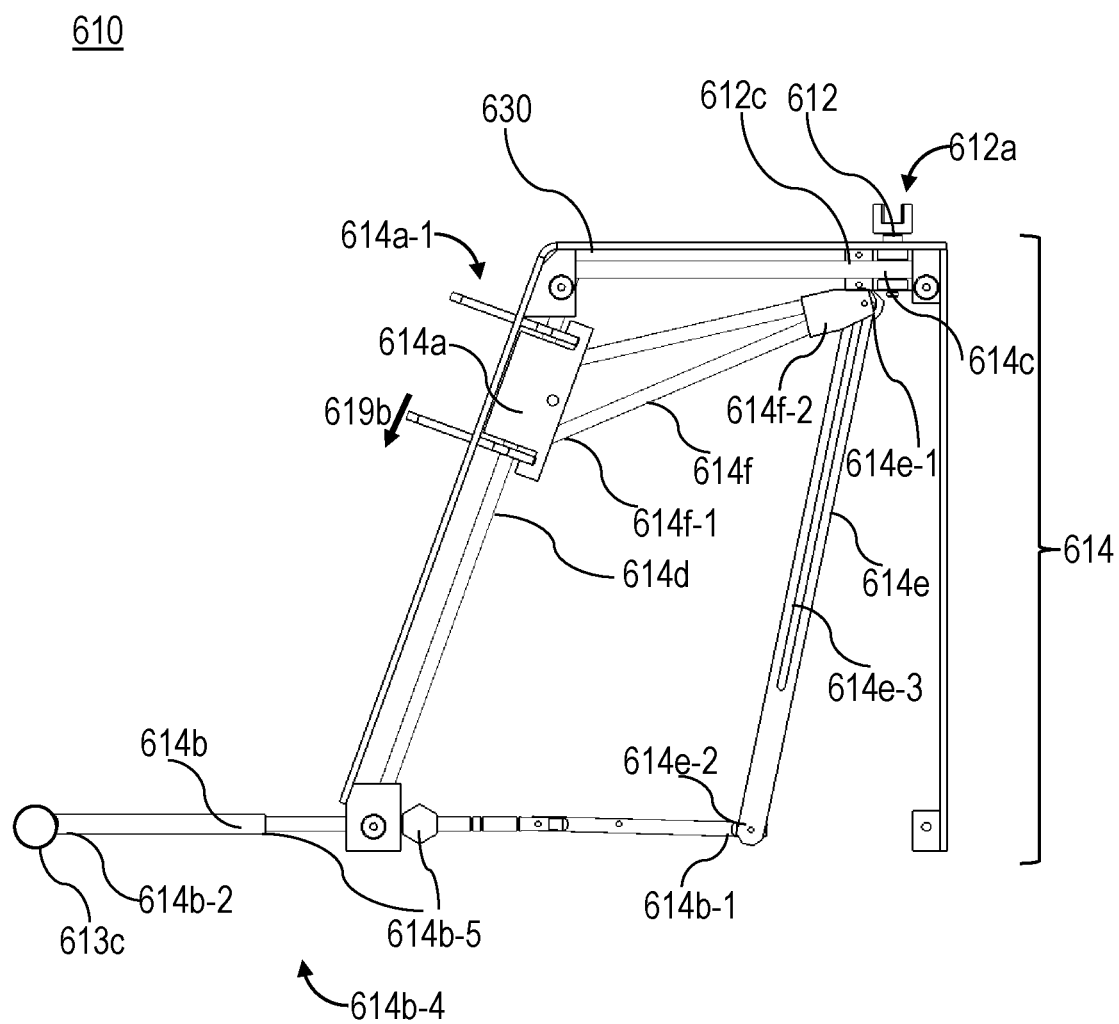
Figure 7D:
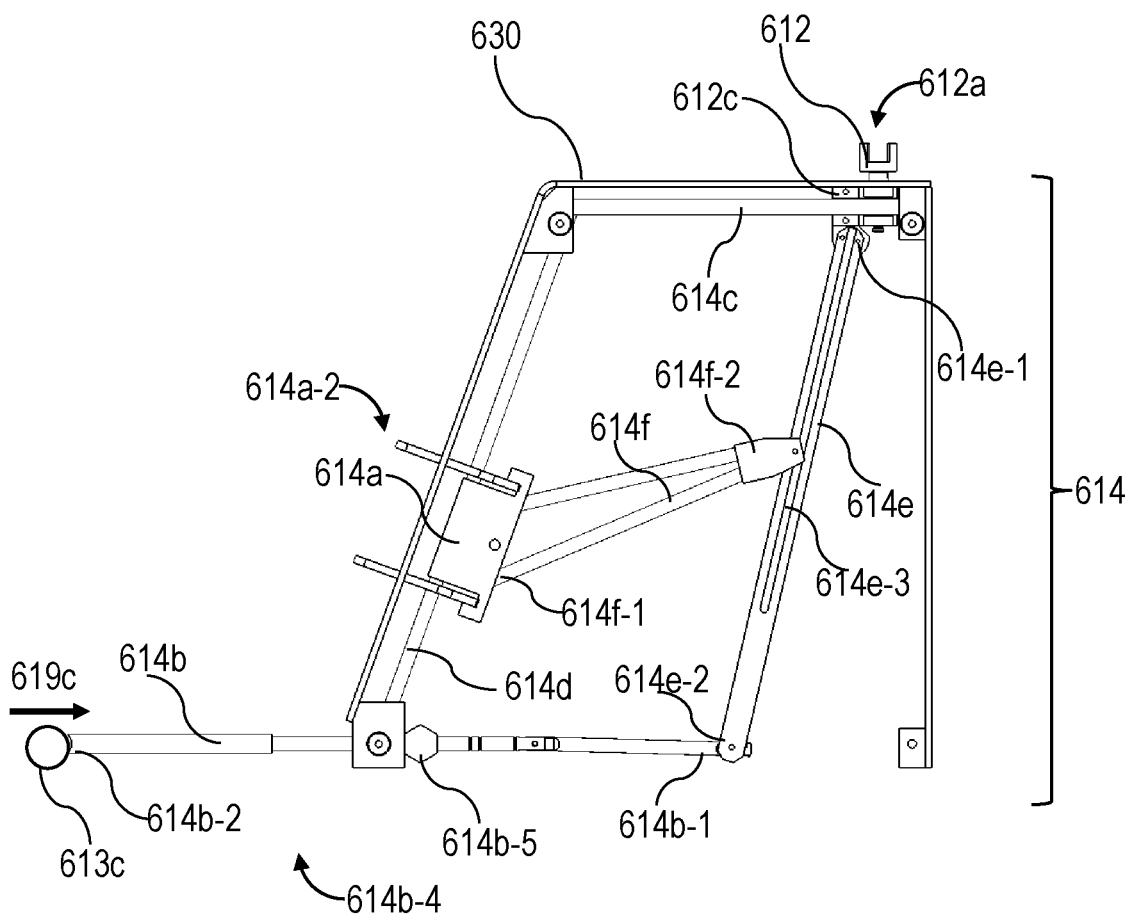

According to some embodiments, second rail 614*d* of each of driving assemblies 614 may be coupled at its ends to housing 630 and may be aligned parallel to rotatable arm 614*e* when respective actuation arm 614*b* is fully extended (e.g., as shown in FIG. 7C).

According to some embodiments, mover 614*a* of each of driving assemblies 614 may be movably coupled to second rail 614*d* and may be arranged to move along second rail 614*d* between its respective initial position 614*a*-1 and respective at least one another position 614*a*-2.

In some embodiments, mover 614*a* of each of driving assemblies 614 may be moved manually by the user of bending device 600. In some embodiments, mover 614*a* of each of driving assemblies 614 may include an affixing mechanism (e.g., spring-loaded affixing mechanism) that may enable motion of the mover when, for example, pressed, and hold the position of the mover when released.

According to some embodiments, rotational axis arm 614*f* of each of driving assemblies 614 may be coupled at its first end 614*f*-1 to respective mover 614*a* and movably coupled at its second end 614*f*-2 to respective rotatable arm 614*e* of respective driving assembly 614.

In some embodiments, second end 614*f*-2 of rotational axis arm 614*f* of each of driving assemblies 614 may be arranged to at least partly embrace respective rotatable arm 614*e* and to move within dents 614*e*-3 on respective rotational arm 614*e*. Dents 614*e*-3 of rotational arm 614*e* of each of driving assemblies 614 may initiate at first end 614*e*-1 of rotational arm 614*e* and may extend towards second end 614*e*-2 of rotational arm 614*e* along at least a portion and along at least one of sides of rotational arm 614*e*.

According to some embodiments, a position of second end 614*f*-2 of rotational axis arm 614*f* of each of driving assemblies 614 (dictated by positions 614*a*-1, 614*a*-2 of respective mover 614*a*) may define a rotational axis about which respective rotational arm 614*e* will rotate upon actuation by respective actuation arm 614*b*.

Figure 7E:
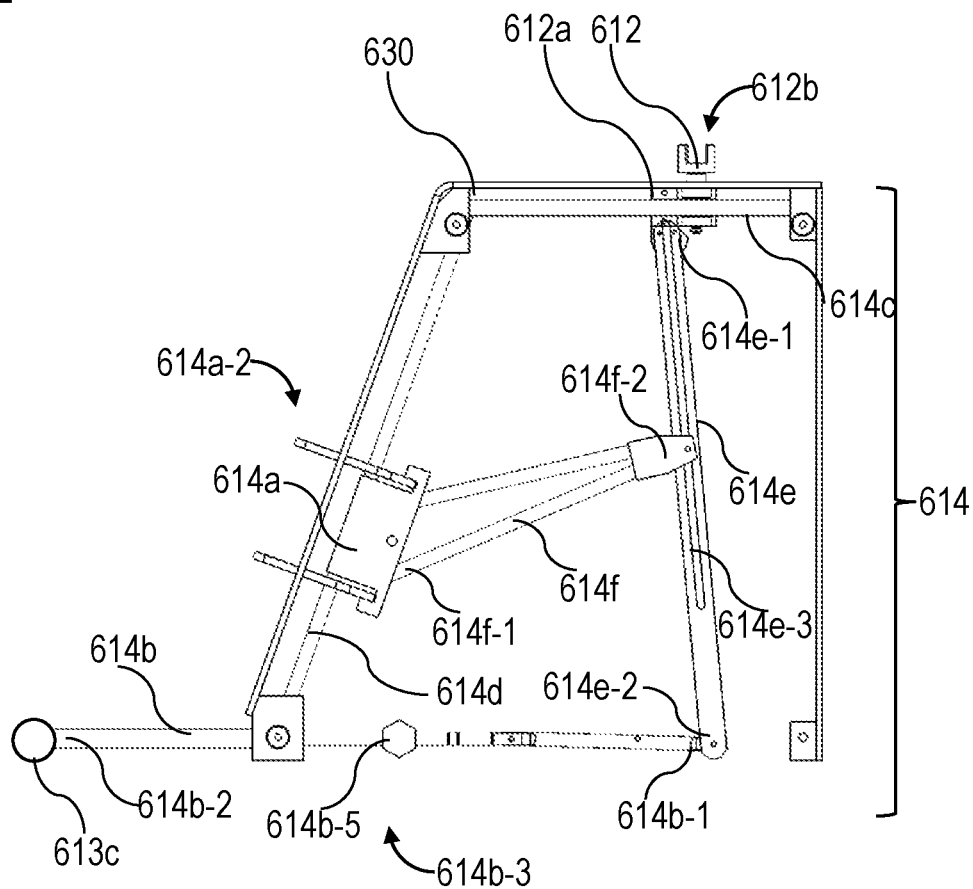

For example, movement of actuation arm 614*b* of each of driving assemblies 614 between its extended and initial positions 614*b*-4, 614*b*-3 may move second end 614*e*-2 of respective rotatable arm 614*e*, thereby rotating respective rotatable arm 614*e* about the rotational axis defined by second end 614*f*-2 of respective rotational axis arm 614*f* and moving respective receiving member 612 along respective first rail 614*c* into one of its other positions 612*b* (e.g., as shown in FIG. 7E).

In some embodiments, the length of first rail 614*c*, the length of rotational axis arm 614*f*, angle 614*d*-1 and angle 614*f*-3 of each of driving assemblies 614 are determined to ensure that second end 614*f*-2 of respective rotational axis arm 614*f* is adjacent to first end 614*e*-1 of respective rotatable arm 614*e* when respective mover 614*a* is in its initial position 614*a*-1, thereby ensuring that respective receiving member 612 remains in its initial position 612*a* independent of movement of respective actuation arm 614*b*.

In some embodiments, the length of first rail 614*c*, the length of rotational axis arm 614*f*, angle 614*d*-1 and angle 614*f*-3 of each of driving assemblies 614 are determined to ensure that respective rotatable arm 614*e* is parallel (or substantially parallel) to respective second rail 614*d* when respective actuation arm 614*b* in in its extended position 614*b*-4.

An offset of the rotational axis of rotational arm 614*e* of each of driving assemblies 614 with respect to first end 614*e*-1 defined by the position of second end 614*f*-2 of respective rotational axis arm 613*d*, which in turn is defined by the position 614*a*-2 of respective mover 614*a*, dictates/defines the measure of movement of respective receiving member 612 with respect to its initial position 612*a*. The larger the offset of the rotational axis of rotational arm 614*e*, the larger the measure movement/displacement of receiving member 612.

In this manner, position 614*b*-2 of movers 614*b* of bending units 610 dictate/define the measure of movement of respective receiving members 612.

According to some embodiments, bending device 600 may be easily pre-set in order to bend the elongated assembly and particularly elongated element 90 disposed therein into the desired shape. The description below (yet made with respect to FIGS. 7B-7E) provides an exemplary method of pre-setting of bending device 600. In various embodiments, the method thereof need not move through each stage or in exactly the same order as described.

At a first stage, actuator arms 614*b* of all driving assemblies 614 of all bending units 610 may be moved from their initial positions 614*b*-1 to their extended positions 614*b*-2. This may be done by, for example, pulling actuation rod 613*c* (e.g., that connects actuator arms 614*b* of driving assemblies 614 of all bending units 610) away from housing 630 of bending device 600 (e.g., as indicated by arrow 619*a* in FIG. 7B).

At the next stage, the position of movers 614*a* of each of driving assemblies 614 of each of bending units 610 may be set to define/dictate the measure of movement of receiving members 612 of respective bending units 610, based on the desired bending profile of elongated element 90 (e.g., as indicated by arrow 619*b* in FIG. 7C).

For example, movers 614*a* of driving assemblies 614 of some of bending units 610 may be moved from their initial positions 614*a*-1 to one of their other positions 614*a*-2 to define the measure of movement of receiving members 612 of the respective some bending units thereof upon actuation. Yet, in this example, movers 614*a* of driving assemblies 614 of other bending units 610 may remain at their initial positions 614*a*-1 in order to ensure that receiving members 612 of the respective other bending units thereof will remain stationary in their initial positions 612*a* upon the actuation.

In some embodiments, scale markings may be made on housing 630 adjacent to movers 612*a* of bending units 610 in order to enable easy operation and setting of movers' 612*a* position.

At the next stage, heated elongated assembly may be positioned within receiving members 612 of bending units 610. The elongated assembly is not shown in FIGS. 7A-7E for sake of clarity.

Alternatively, the elongated assembly may be heated upon positioning thereof within bending device 600, for example using infrared or laser radiation.

At the next stage, actuation rod 613*c* that connects actuation arms 614*b* of all driving assemblies 614 of all bending units 610 may be pushed toward housing 630 of bending device 600 (e.g., as indicated by arrow 619*c* in FIG. 7D), thereby adjusting the position of receiving members 612 of all bending units 610 as defined/dictated by the positions of movers 614*a* of respective bending units 610 and bending the elongated assembly and particularly elongated element 90 disposed therein into the desired shape (e.g., as shown in FIG. 7E).

In this manner, bending device 600 may be easily pre-set to bend the elongated assembly and elongated element 90 disposed therein into the desired bending shape.

According to some embodiments, the entire bending device 600 (e.g., described above with respect to FIGS. 7A-7E) may be sterilized before/after each operational procedure.

Figure 8A:
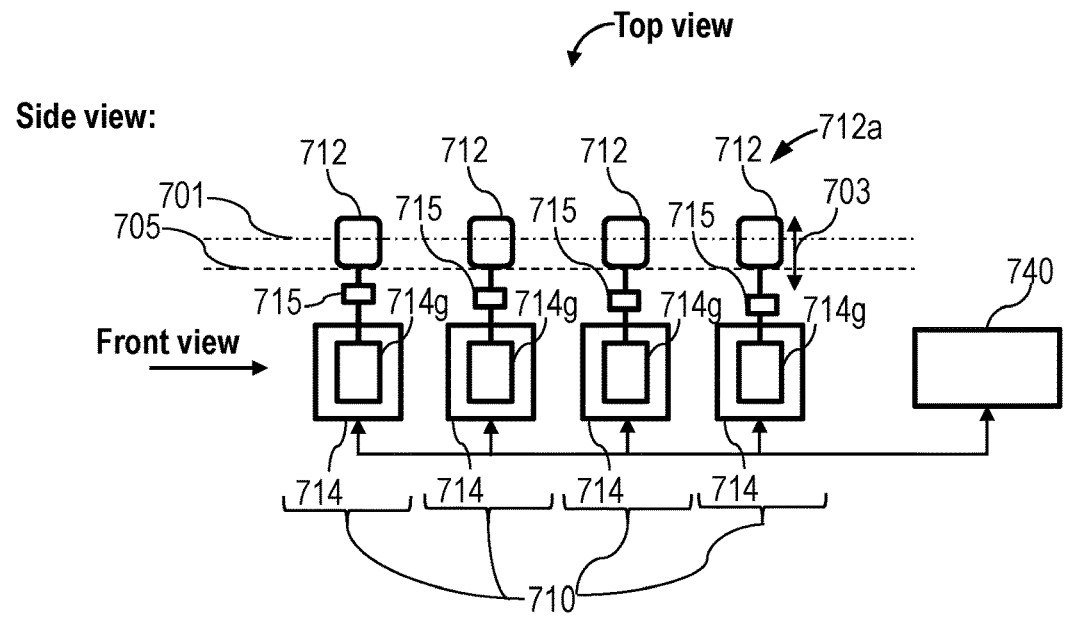
FIG. 8A which is a schematic illustration of a bending device for bending an elongated assembly with bending units having motorized driving assemblies, according to some embodiments of the invention.
Figure 8A:
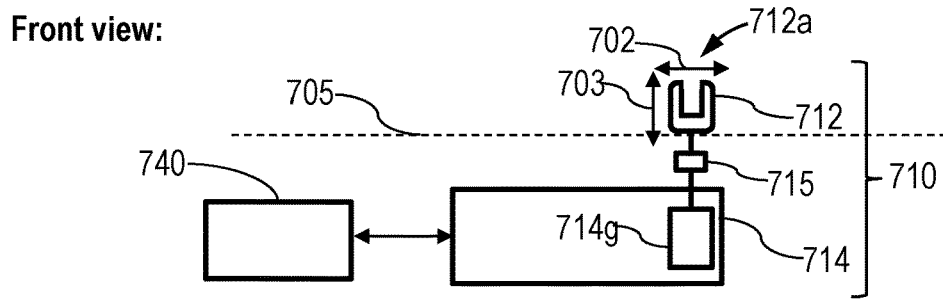
Figure 8A:
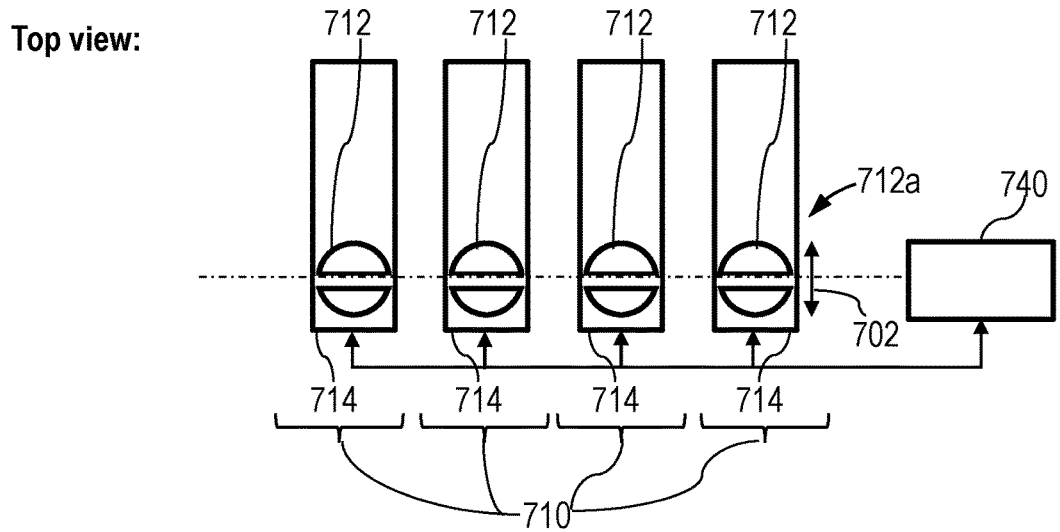

Reference is now made to FIGS. 8A, which is a schematic illustration of a bending device 700 for bending an elongated assembly with bending units 710 having motorized driving assemblies 714, according to some embodiments of the invention.

According to some embodiments, bending device 700 includes multiple bending units 710 and a controller 740 (e.g., as shown in FIG. 8A).

Each of bending units 710 may include receiving member 712 arranged to receive a portion of an elongated assembly and motorized driving assembly 714 arranged to move receiving member 712 of respective bending unit 710 between its respective initial position 712*a* and at least one other position 712*b* based on the desired bending profile of elongated element 90.

In some embodiments, bending units 710 (e.g., receiving members 712 and driving assemblies 714) of device 700 may be similar to bending units 510 (e.g., receiving members 512 and driving assemblies 514) as described above with respect to FIGS. 6A-6C.

Each of driving assemblies 714 of each of bending units 710 may include at least one motor 714g (e.g., as shown in FIG. 8A). For example, motor 714g may be rotating motors. Receiving member 712 of each of bending units 710 may be coupled to motor 714g of respective driving assembly 714 using, for example, a transmission sub-unit 715. Transmission sub-unit 715 of each of bending units 710 may be arranged to, for example, transmit rotations generated by motor 714g of respective driving assembly 714 into translational movement of receiving member 712 of respective bending unit 710.

Controller 740 may be coupled to driving assemblies 714 of all bending units 710 and may be configured to control the operation of driving assemblies 714 and to thus control the movement/displacement of receiving members 712 of all bending units 710 in first direction 702 and/or in second direction 702 based on the desired bending profile.

In some embodiments, controller 740 may be configured to limit the measure of movement of adjacent receiving members 712 with respect to each other, thereby limiting the bending radius of the elongated assembly and elongated element 90 disposed therein in the bending region thereof and ensuring that the bending radius does not exceed the predetermined minimum bending radius value (e.g., 45 mm).

In some embodiments, motors 714g may be sterilizable motors. In this manner, the entire bending device 700 (e.g., described above with respect to FIG. 8A) may be sterilized before/after each operational procedure.

Reference is now made to FIGS. 8B, 8C, 8D and 8E which are schematic illustrations of a single motorized bending unit 710 of a bending device 700 for bending an elongated assembly, according to some embodiments of the invention.

Figure 8B:
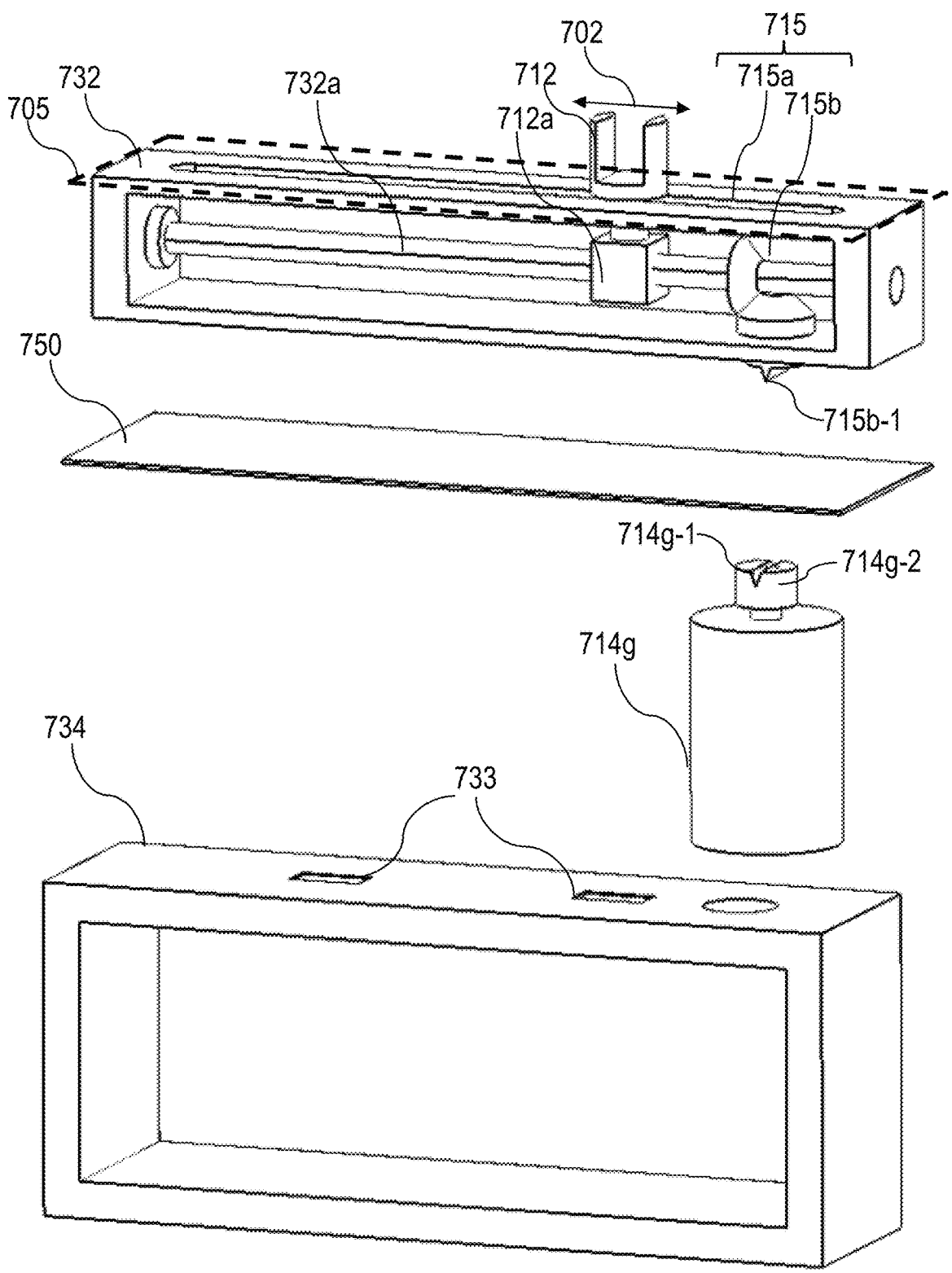
FIGS. 8B, 8C, 8D and 8E are schematic illustrations of a single motorized bending unit of a bending device for bending an elongated assembly, according to some embodiments of the invention.
Figure 8C:
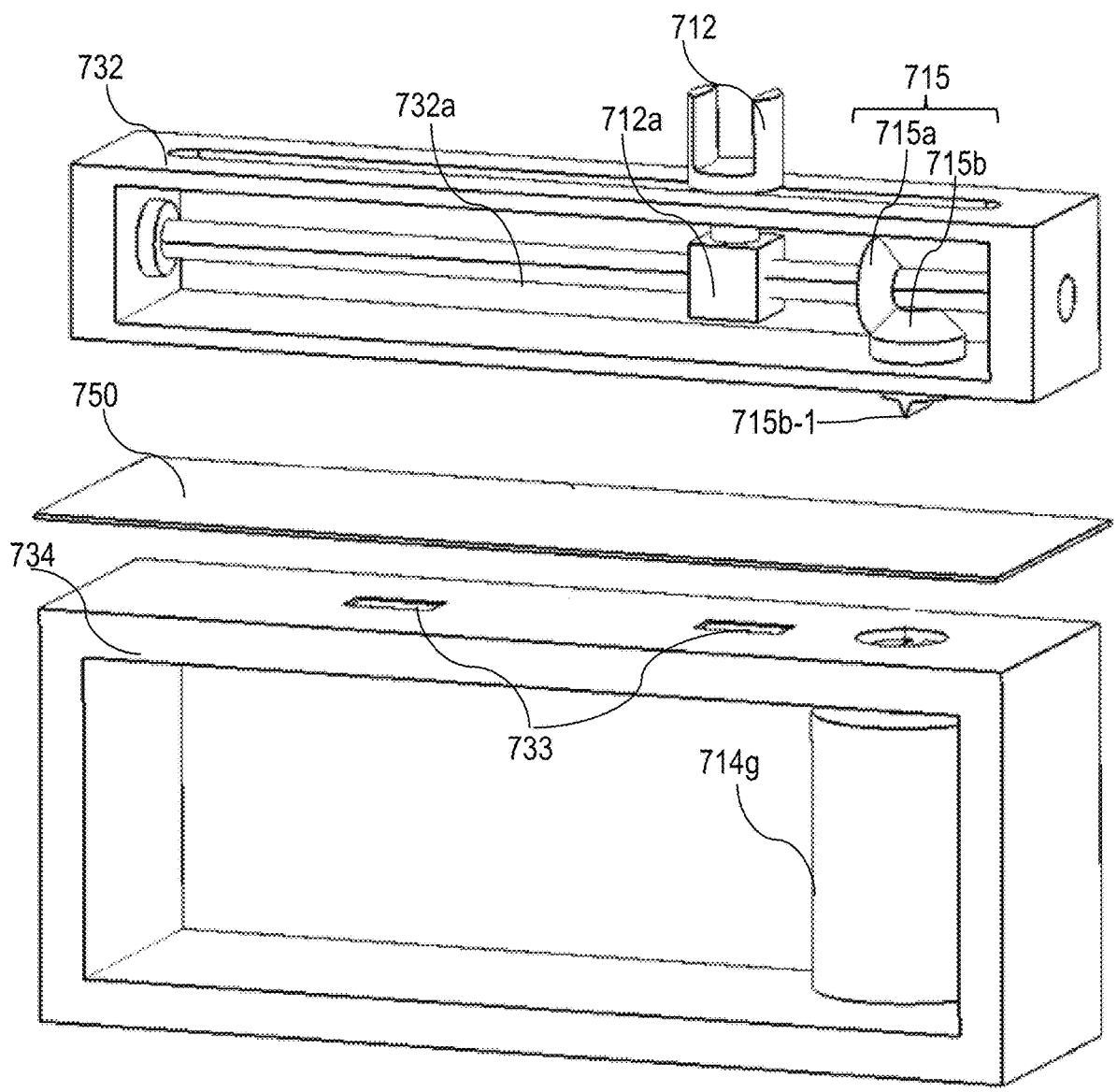
Figure 8D:
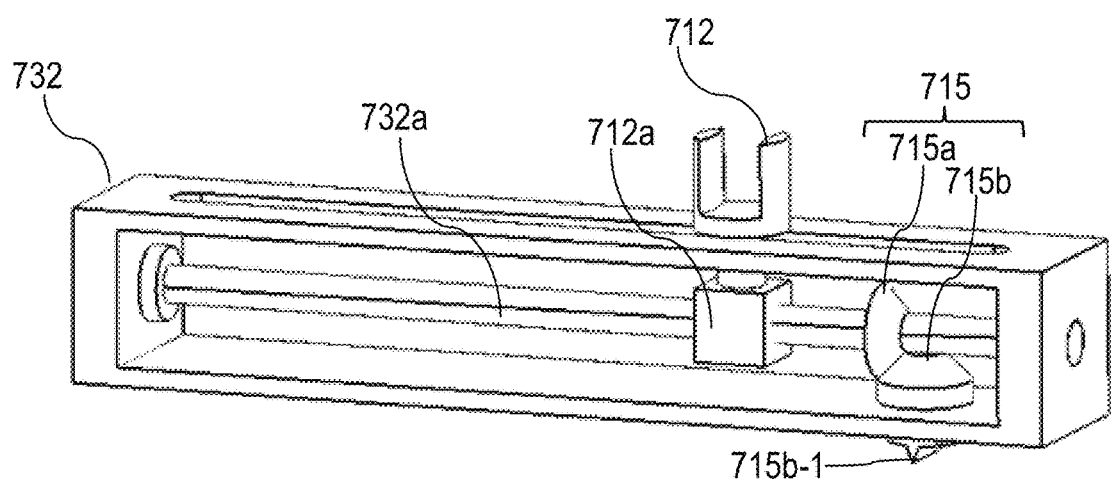
Figure 8D:
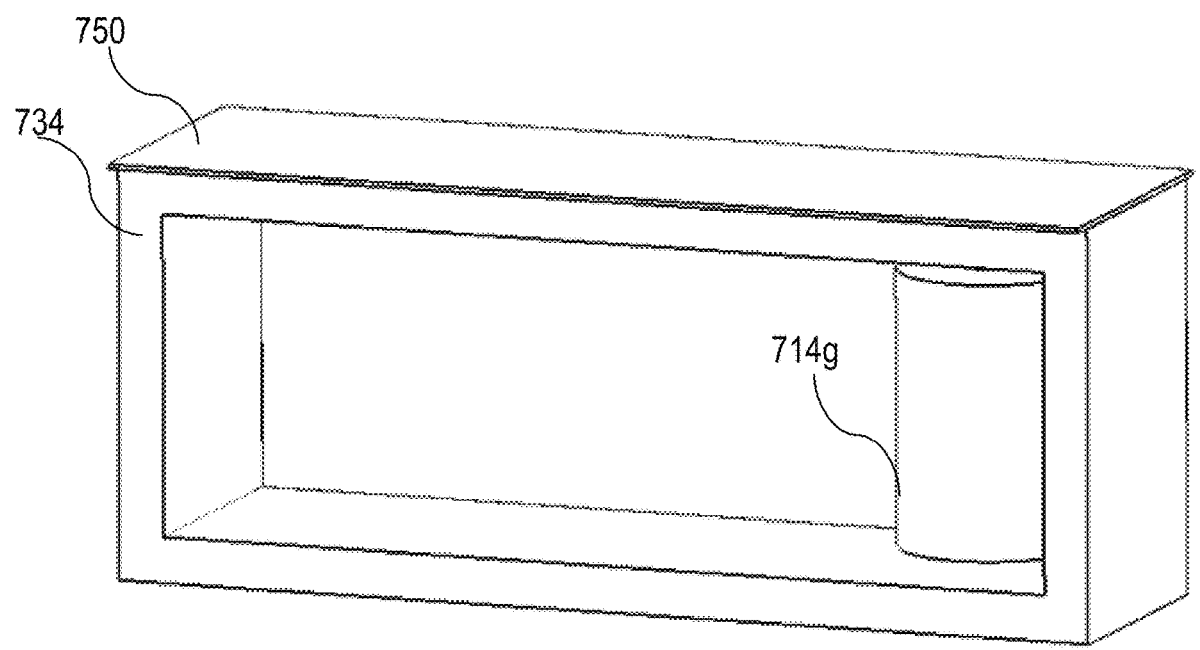
Figure 8E:
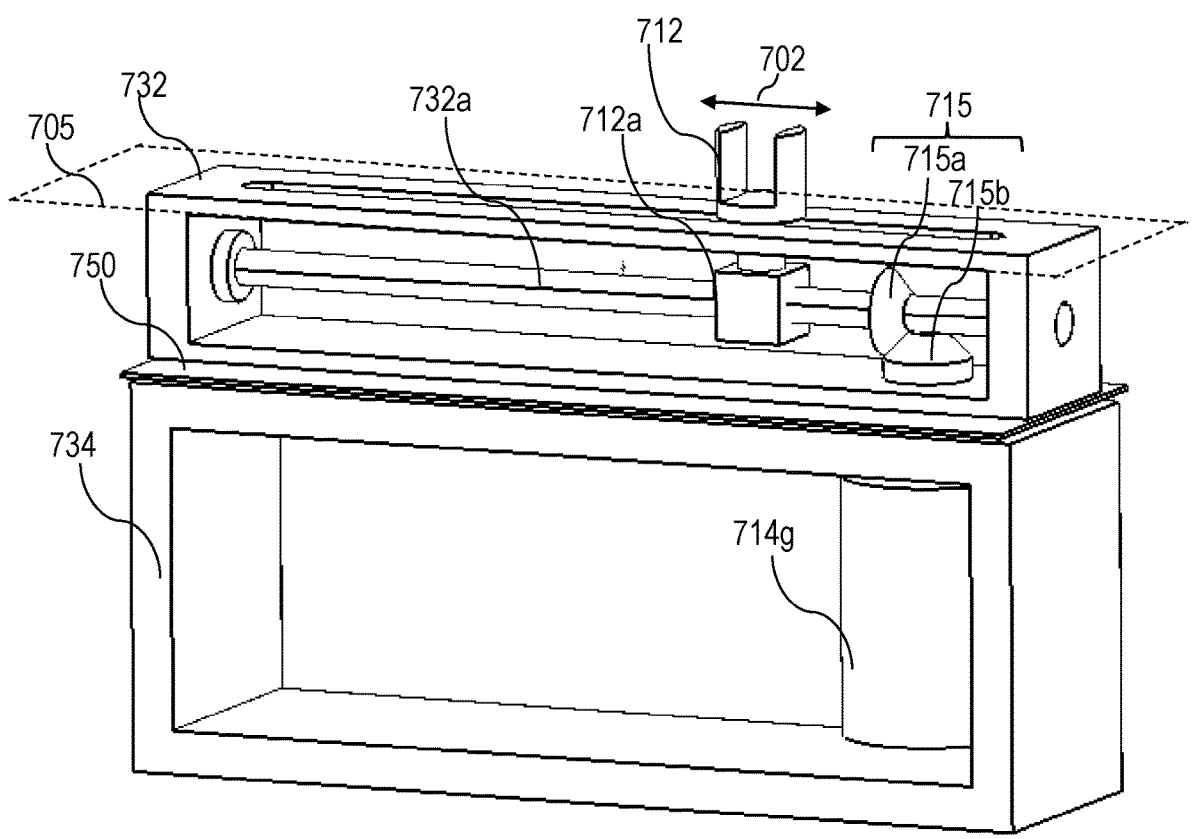

FIG. 8B shows an exploded view of bending unit 710. FIG. 8C and FIG. 8D show disassembled views of bending unit 710. FIG. 8E shows an assembled view of bending unit 710.

According to some embodiments, bending device 700 includes a receiving members housing 732 arranged to accommodate receiving members 712 of all bending units 710 and a driving assemblies housing 734 arranged to accommodate driving assemblies 714 of all bending units (e.g., as shown in FIGS. 8B-8E). FIGS. 8B-8E show single bending units 710 for sake of clarity. It is noted that other bending units 710 may have a similar structure and operate in a similar way.

Receiving members housing 732 and driving assemblies housing 734 may be detachably couplable. In some embodiments, at least one of receiving members housing 732 and driving assemblies housing 734 may include at least one magnet 733 (e.g., as shown in FIGS. 8B and 8C). Magnets 733 may ensure tight contact/coupling of receiving members housing 732 with driving assemblies housing 734 yet enabling easy detachment thereof.

According to some embodiments, each of bending units 710 may include a rod 732a attached at its end within receiving member housing 732 parallel to plane 705 and aligned in first direction 702 (e.g., as shown in FIGS. 8B-8E). Receiving member 712 of each of bending units 710 may be movably coupled to respective rod 732a and arranged to move along respective rod 732 in first direction 702. In some embodiments, each of rods 732a includes a thread along the entire length of rods 732a.

In some embodiments, transmission sub-unit 715 of each of bending units 710 may be located in receiving members housing 732. Transmission unit 715 of each of bending units 710 may, for example, include a first gear 715a mounted on respective third rail 732a and a second gear 715b perpendicular to first gear 715a and detachably couplable to motor 714g of respective driving assembly 714 (e.g., as shown in FIGS. 8B-8E).

For example, second gear 715b of transmission sub-unit 715 of each of bending units 710 may include a protrusion 715b-1 and motor 714g of respective driving assembly 714 may include a mating indent 714g-1 on a motor-connector 714g-2. Protrusion 715b-1 of second gear 715b of transmission sub-unit 715 of each of bending units 710 may enter indent 714g-1 of motor 714g of respective driving assembly 714 when receiving members housing 732 is coupled to driving assemblies housing 734.

Transmission sub-unit 715 of each of bending units 710 may be arranged to convert rotations generated by motor 714g of respective driving assembly 714 into translation movement of receiving member 712 of respective bending unit 710 in first direction 702. For example, transmission sub-unit 715 of each of bending units 710 may convert rotations generated by motor 714g of respective driving assembly 714 into rotation of respective rod 732a and result in movement of respective receiving member 712 in first direction 702.

According to some embodiments, bending device 700 may include a covering 750. Covering 750 may be, for example, sterile plastic layer and/or fabric and may be arranged to cover driving assemblies housing 734 prior to coupling of receiving members housing 732 thereto. In these embodiments, protrusion 715b-1 of second gear 715b of transmission sub-unit 715 of each of bending units 710 may have a desired measure of sharpness to cut through covering 750 when receiving members housing 732 is being coupled to driving assemblies housing 734.

In these embodiments, driving assemblies 714 (e.g., motors 714g) and driving assemblies housing 734 need not to be sterilized, while receiving members 712 and receiving members housing 732 may be sterilized before/after each operational procedure.

Some embodiments of bending devices, for example those described above with respect to FIGS. 7A-7E and 8B-8E, are capable of bending the elongated assembly and particularly elongated element 90 in a single plane (e.g., planes 605, 705, respectively) and thereby provide two-dimensional bending of elongated element 90. According to some embodiments, bending devices may be capable of bending the elongated assembly and/or elongated element 90 in more than one plane and thus providing three-dimensional bending of elongated element 90 (e.g., as described below with respect to FIGS. 9A and 9B).

Figure 9A:
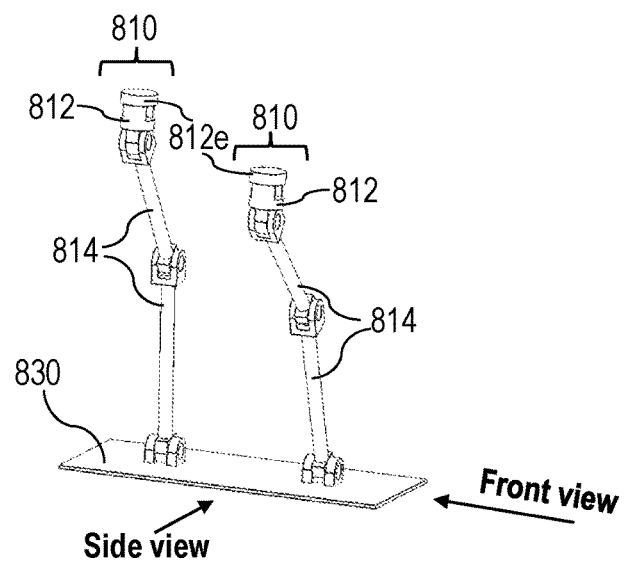
FIGS. 9A and 9B are schematic illustrations of a bending device capable of providing three-dimensional bending of an elongated assembly, according to some embodiments of the invention.
Figure 9A:
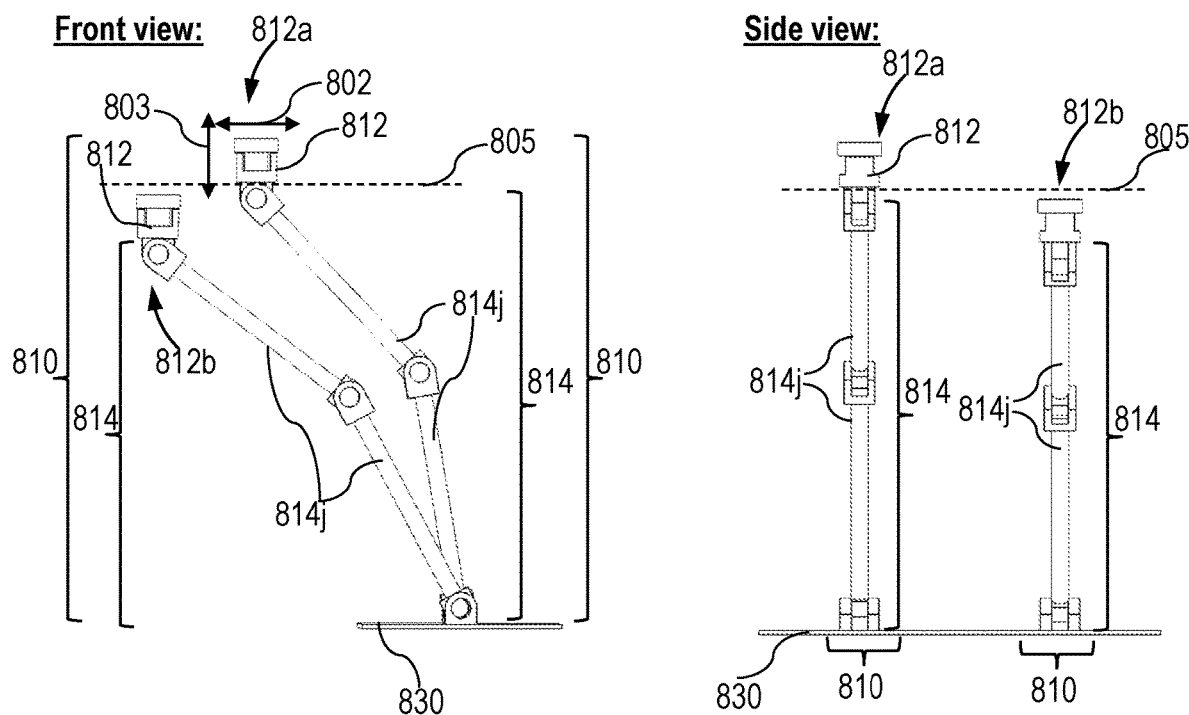
Figure 9B:
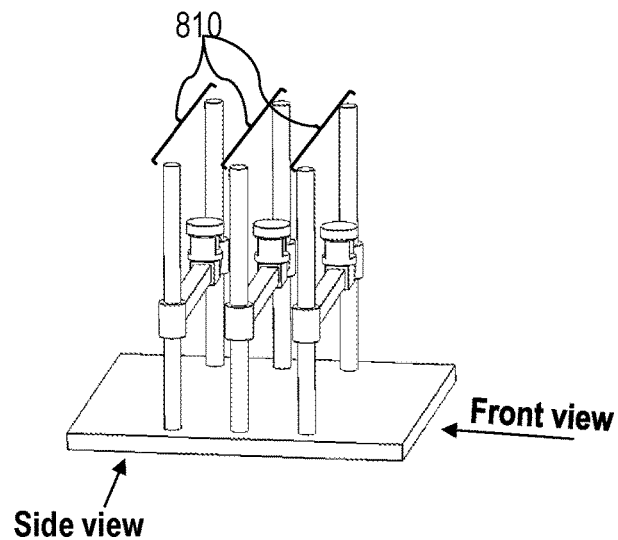
Figure 9B:
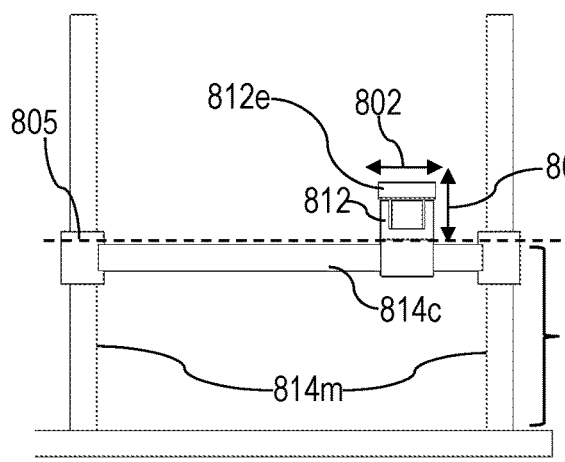
Figure 9B:
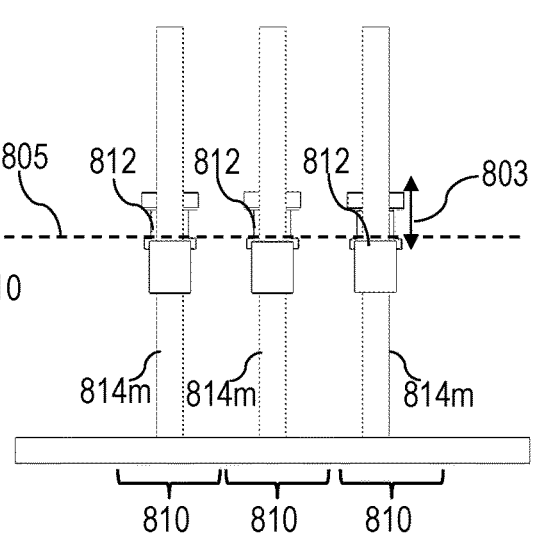

Reference is now made to FIGS. 9A and 9B, which are schematic illustrations of a bending device 800 capable of providing three-dimensional bending of an elongated assembly, according to some embodiments of the invention.

According to some embodiments, bending device 800 includes multiple bending units 810. Each of bending units 810 may include receiving member 812 arranged to receive a portion of the elongated assembly and driving assembly 814 arranged to move receiving member 812 of respective bending unit 810 between its respective initial position 812a and at least one other position 812b based on the desired bending profile of elongated element 90.

In some embodiments, bending units 810 (e.g., receiving members 812 and driving assemblies 814) of device 800 may be similar to bending units 510 (e.g., receiving members 512 and driving assemblies 514) as described above with respect to FIGS. 6A-6C.

According to some embodiments, driving assemblies 814 of bending units 810 may be arranged to move respective receiving members 812 in both first direction 802 (e.g., parallel to plane 805) and in second direction 803.

According to some embodiments, driving assemblies 814 of each of bending units 810 includes an articulated arm 814*j* (e.g., as shown in FIG. 9A). Articulated arm 814*j* of each of driving assembly 814 may be pivotally coupled at its first end to housing 810 and may be pivotally coupled at its second end to receiving member 812 of respective bending unit 810. Articulated arm 814*j* of each of driving assemblies 814 may enable movement of respective receiving member in first direction 802 and/or in second direction 803 (e.g., as shown in FIG. 9A).

According to some embodiments, driving assembly 814 of each of bending units 810 includes a pair of rods 814*m* (e.g., as shown in FIG. 9B). Rods 814*m* of each of driving assemblies 814 may be coupled to housing 830 and extend in second direction 803 that is perpendicular to plane 805.

Receiving member 812 of each of bending units 810 may be movably coupled to first rail 814*c* of respective driving assembly 814 and arranged to move along respective first rail 814*c* in first direction 802. First rail 814*c* of each of driving assemblies 814 may be movably coupled at its ends to respective rods 814*m* and may be arranged to move along respective rods 814*m* in second direction 803. In this manner, receiving member 812 of each of bending units 810 may be moved in both first direction 802 and second direction 803.

According to some embodiments, each of receiving members 812 may include a cap 812*e* arranged to cover respective receiving member 812. Caps 812*e* may be arranged to prevent escaping of the elongated assembly from receiving members 812 during bending.

According to various embodiments, each of driving assemblies 814 of each of bending units 810 described above with respect to FIGS. 9A and 9B may be manually adjustable (e.g., as described above with respect to FIGS. 7A, 7B, 7C, 7D and 7E) or motorized (e.g., as described above with respect to FIGS. 8A, 8B, 8C, 8D and 8E).

Figure 10A:
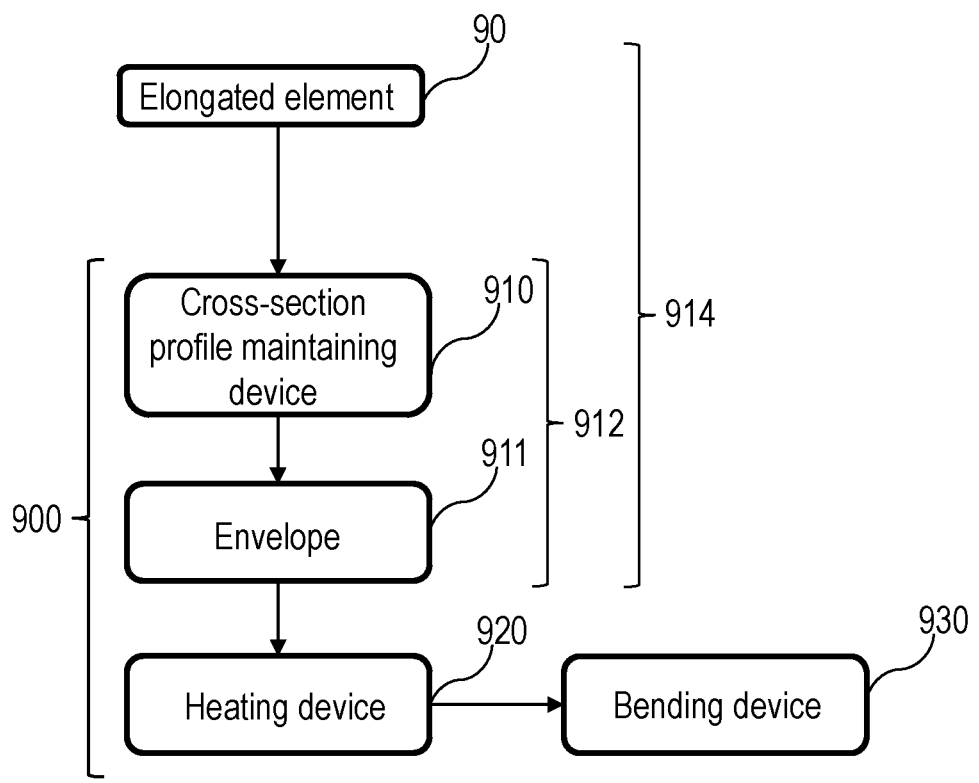
FIG. 10A is a block diagram of a system for bending an elongated assembly, according to some embodiments of the invention.

Reference is now made to FIG. 10A, which is a block diagram of a system 900 for bending an elongated assembly, according to some embodiments of the invention.

According to some embodiments, system 900 may include a device 910 for maintaining a cross-sectional profile of elongated element 90, a heating device 920 and a bending device 930. In some embodiments, system 900 may include an assembly 912 including device 910 and an envelope 911.

Device 910 may receive and tightly support elongated element 90 and prevent distortion of elongated element 90 during bending. In various embodiments, device 910 may be device 100 described above with respect to FIGS. 1A, 1B, 1C, 1D and 1E and FIGS. 2A, 2B, 2C, 2D, 2E and 2F, device 200 as described above with respect to FIGS. 3A, 3B, 3C and 3D, and/or device 300 as described above with respect to FIG. 4.

In various embodiments, elongated element 90 and/or elongated element 90 supported within device 910 may be accommodated within envelope 911, thus providing an elongated assembly 914. Envelope 911 may, for example, be envelope 330, envelope 340 or envelope 350 described above with respect to FIGS. 4A, 4B and 4C, respectively.

Heating device 920 may receive elongated assembly 914 and elevate a temperature of elongated element 90 disposed therein up to the predetermined temperature pressure (e.g., 380° C.). In some embodiments, heating device 920 may be heating device 400 described above with respect to FIG. 5.

Bending device 930 may receive elongated assembly 914 and bend elongated assembly 914, and particularly elongated element 90 disposed therein, based on the predetermined bending profile. In some embodiments, bending device 930 may be any of bending devices described above with respect to FIGS. 6A, 6B and 6C, FIGS. 7A, 7B, 7C, 7D and 7E, FIGS. 8A, 8B, 8C, 8D and 8E, and FIGS. 9A and 9B.

Figure 10B:
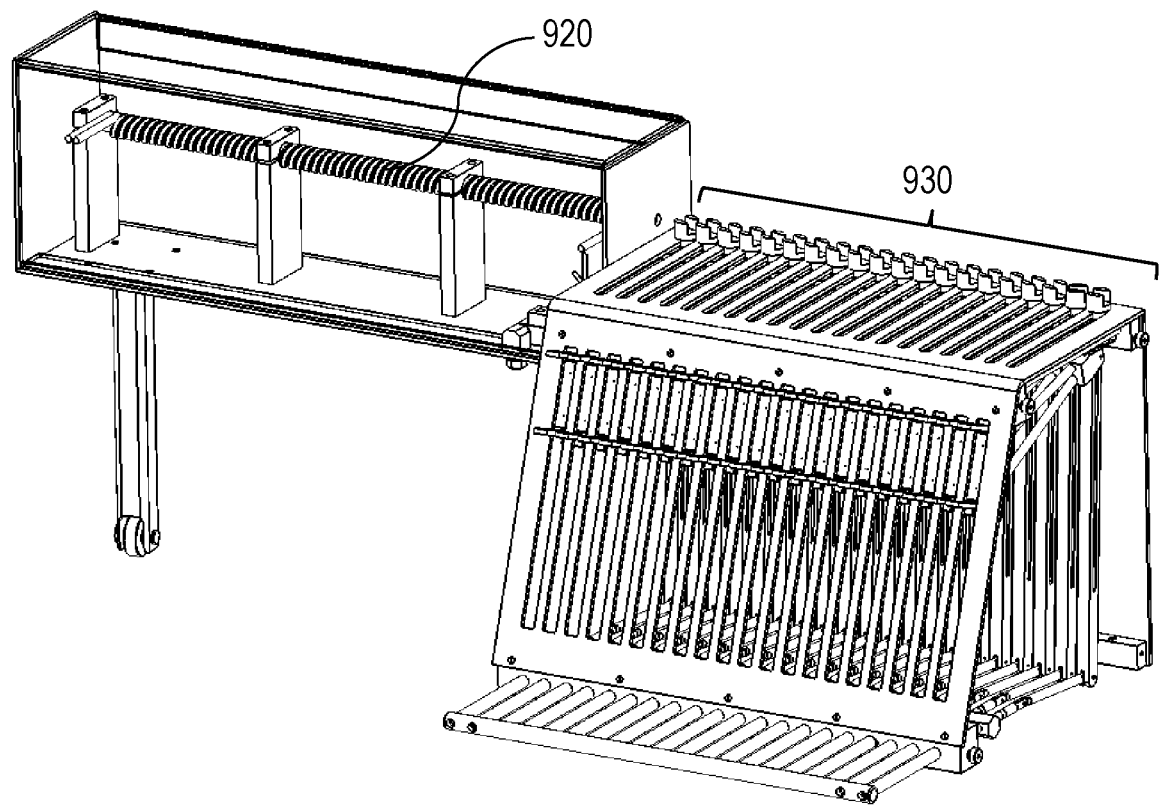
FIGS. 10B and 10C are schematic illustrations of various configurations of coupling of a heating device and a bending device, according to some embodiments of the invention.
Figure 10C:
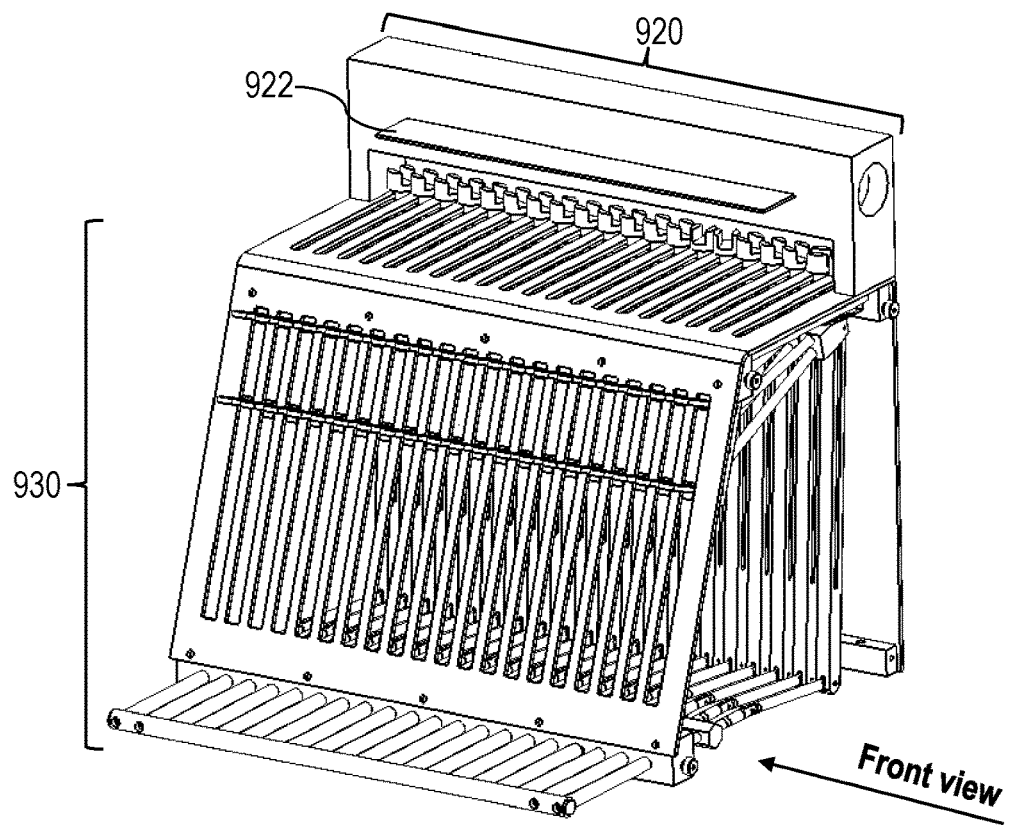
Figure 10C:
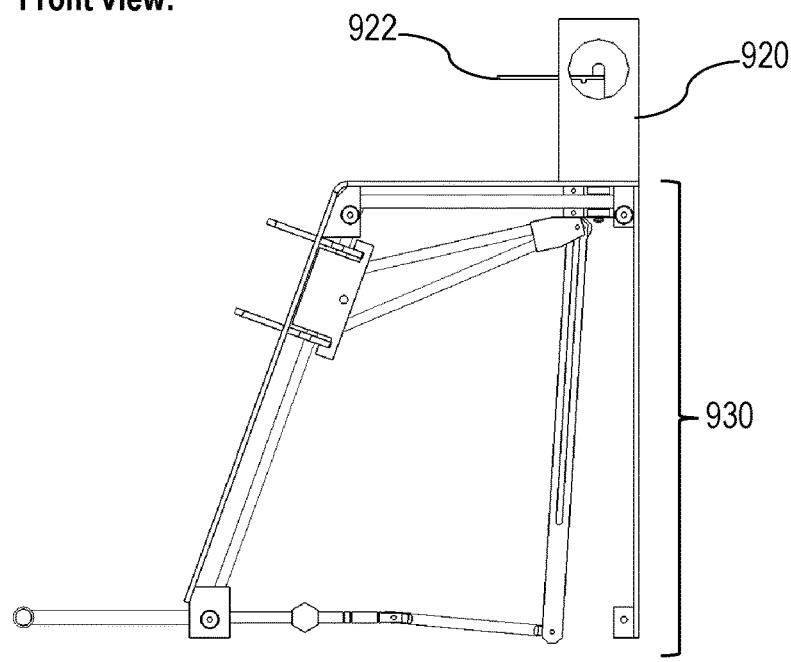

Reference is now made to FIGS. 10B and 10C, which are schematic illustrations of various configurations of coupling of a heating device 920 and a bending device 930, according to some embodiments of the invention.

According to some embodiments, heating device 920 may be positioned adjacent to bending device 930 at a height that enables pulling elongated assembly 914 from heating device 920 into bending device 930 (e.g., as shown in FIG. 10B).

According to some embodiments, heating device 920 may be positioned above bending device 930 (e.g., as shown in FIG. 10C). In these embodiments, heating device 920 may include a supporting plate 922. Supporting plate 922 may support elongated assembly 914 when accommodated within heating device 920. Upon heating of elongated element 90 to the predetermined temperature value, supporting plate 922 may be removed, thereby letting elongated assembly to fall into bending device 930.

It is noted that, although FIGS. 10B and 10C show bending device 930 similar to that described above with respect to FIGS. 7A-7E, any bending device of those described above with respect FIGS. 6A, 6B and 6C, FIGS. 7A, 7B, 7C, 7D and 7E, FIGS. 8A, 8B, 8C, 8D and 8E, and FIGS. 9A and 9B may be used.

Figure 11:
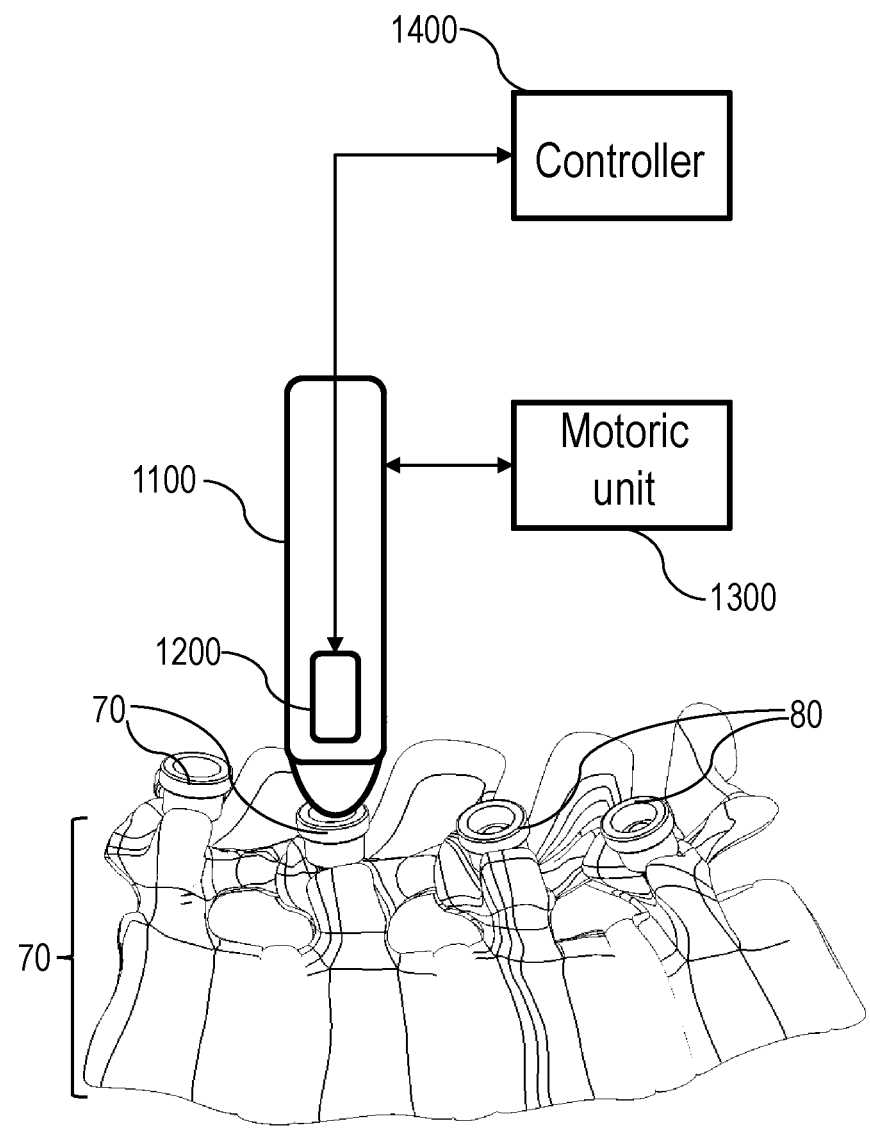
FIG. 11 is a schematic illustration of a device for determining a desired bending profile of an elongated element, according to some embodiments of the invention.

Reference is now made to FIG. 11, which is a schematic illustration of a device 1000 for determining a desired bending profile of an elongated element 90, according to some embodiments of the invention.

According to some embodiments, device 1000 includes a housing 1100 and at least one sensor 1200 embedded in housing 1100 (e.g., as shown in FIG. 11). Sensor(s) 1200 may be capable of determining locations of target zones 70. In some embodiments, sensor(s) 1200 may include at least one of: GPS, accelerometer, gyro, electromagnetic field sensor, hall sensor, LIDAR, Radar, or any combination thereof.

When elongated element 90 is an implant, target zones 70 may, for example, be points of connection of the implant (e.g., elongated element 90) to anatomical zone 70. For example, FIG. 11 shows spinal segments as an example of anatomical zone 70 and pedicle screws as an example of target zones 70. In this example, pedicle screws (e.g., target zones 70) are arranged to receive and support a rod (e.g., elongated element 90) that has to be bent to accurately mimic the geometry of anatomical zone 70.

According to some embodiments, housing 1100 may be a hand-held device and may be manually operated by the user (e.g., by the surgeon).

According to some embodiments, device 1000 include a motoric unit 1300 mechanically coupled with housing 1100. Motoric unit 1300 may be arranged to operate (e.g., move) housing 1100.

In order to obtain data concerning the locations of target zones 70, housing 1100 (e.g., operated by the user or by motoric unit 1300) may subsequently touch each of target zones 70, and sensor(s) 1200 may generate the data concerning the locations of target zones 70.

According to some embodiments, device 1000 may include a controller 1400. Controller 1400 may be in communication (e.g., wired or wireless) with sensor(s) 1200 and may be configured to receive from sensor(s) 1200 the data concerning the locations of target zones 70.

In some embodiments, controller 1400 may be configured to determine, based on the data concerning the locations of target zones 70, the desired bending profile of elongated element 90.

In some embodiments, controller 1400 may be in communication with a controller of a bending device (e.g., such as controller 740 of bending device 700 as described above with respect to FIG. 8A). Controller 1400 may be configured to transmit the desired bending profile to the controller of the bending device, which may be configured to operate the bending units of the bending device (e.g., such as bending units 710 as described above with respect to FIG. 8A-8E) to bend elongated element 90 based on the desired bending profile thereof.

In some embodiments, the data concerning the locations of target zones 70 may be transmitted to the controller of the bending device, and the controller of the bending device may be further configured to determine the desired bending profile based on the data thereof.

In some embodiments, controller 1400 may generate an output including instructions concerning manual operation of the bending units of the bending device (e.g., such as bending device 600 described above with respect to FIGS. 7A-7E).

According to some embodiments, device 1000 may be part of a system for bending elongated element 90 (e.g., such as system 900 described above with respect to FIGS. 10A-10C).

Alternatively or complementarily, the desired bending profile of elongated element 90 may be determined by any imaging system such as, for example, computed tomography (CT), magnetic resonance imaging (MRI), X-Ray, navigation system, etc., prior to and/or during the operational procedure.

Alternatively or complementarily, a deformable template may be used to determine the desired bending profile of elongated element 90. The deformable template may, for example, have shape and dimensions that may be similar to shape and dimensions of elongated element 90. The template may be manually deformed by the user to pass through target zones 70 and fit anatomical zone 70. The deformed template may be then positioned in the bending device the bending units of which may then be operated according to the deformed template.

Figure 12:
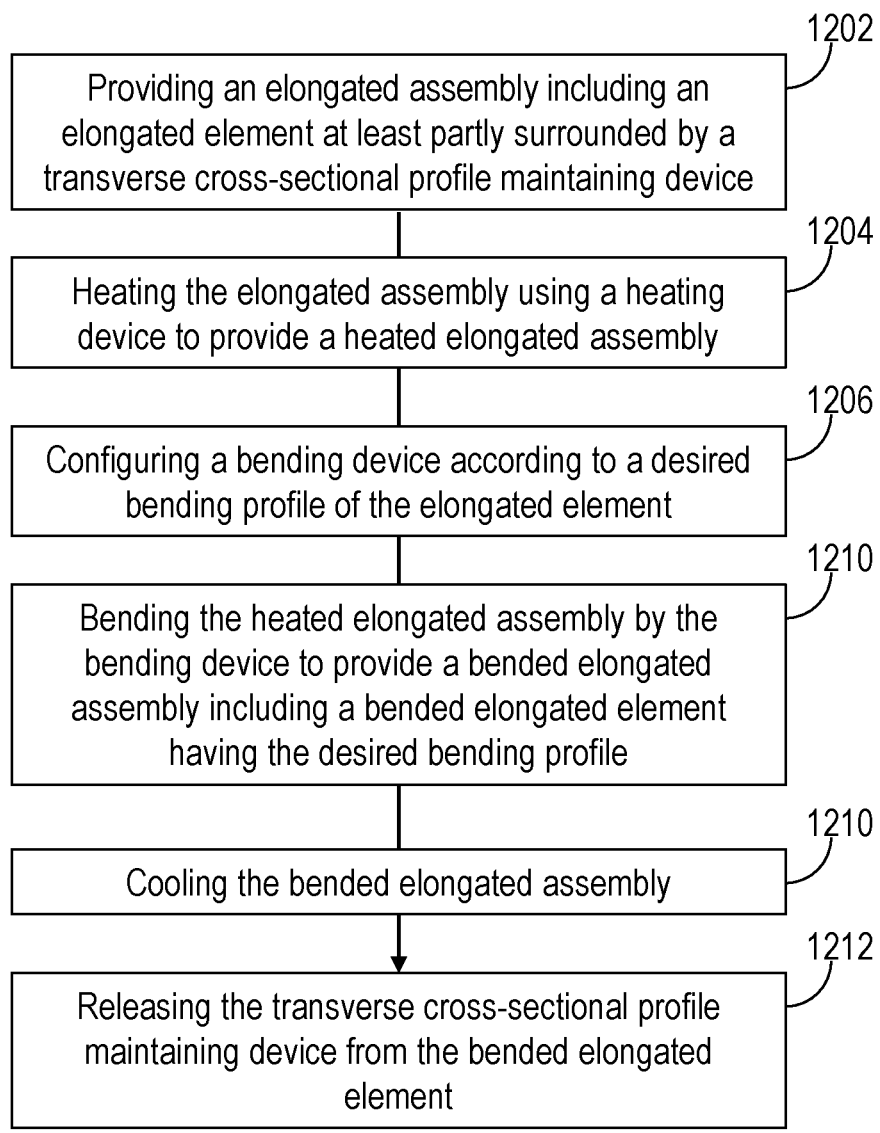
FIG. 12 is a flowchart of a method of bending of an elongated assembly, according to some embodiments of the invention.

Reference is now made to FIG. 12, which is a flowchart of a method of bending of an elongated assembly, according to some embodiments of the invention.

It is noted that the method is not limited to the flowcharts illustrated in FIG. 12 and to the corresponding description. For example, in various embodiments, the method need not move through each illustrated box or stage, or in exactly the same order as illustrated and described.

Some embodiments may include providing an elongated assembly, which elongated assembly may include an elongated element at least partly surrounded by a transverse cross-sectional profile maintaining device (stage 1202).

The elongated assembly may be similar to elongated assembly 80 described hereinabove. The elongated element may be similar to elongated element 90 described hereinabove. For example, the elongated element may be an elongated orthopedic implant. The transverse cross-sectional profile maintaining device may be similar to, for example, device 100 described above with respect to FIGS. 1A-1E, FIGS. 2A-2F and device 200 described above with respect to FIGS. 3A-3B.

Some embodiments may include heating the elongated assembly using a heating device to provide a heated elongated assembly (stage 1204). The heating device may be similar to heating device 400 described above with respect to FIG. 5.

Some embodiments may include configuring a bending device according to a desired bending profile of the elongated element (stage 1206).

The bending device may be similar to, for example, bending device 500 described above with respect to FIGS. 6A-6C, bending device 600 described above with respect to FIGS. 7A-7E, bending device 700 described above with respect to FIGS. 8A-8E, and bending device 800 described above with respect to FIGS. 9A-9B.

The desired bending profile may be predetermined using, for example, device 1000 described above with respect to FIG. 11, an imaging system (e.g., CT, MRI, X-Ray, etc.) or a deformable template.

Some embodiments may include bending the heated elongated assembly by the bending device to provide a bended elongated assembly including a bended elongated element having the desired bending profile (stage 1208). For example, as described above with respect to any one of FIGS. 6A-6C, FIGS. 7A-7E, FIGS. 8A-8E and FIGS. 9A-9B.

Some embodiments may include cooling the bended elongated assembly (stage 1210). The cooling may be, for example, active. In another example, the cooling may be passive.

Some embodiments may include releasing the transverse cross-sectional profile maintaining device from bended elongated element (stage 1212). For example, as described above with respect to any one of FIGS. 1A-1E, FIGS. 2A-2F and FIGS. 3A-3B.

In some embodiments, the elongated assembly, the heating device and the bending device may be sterile and sterilizable. For example, the heating device may include a heating envelope (e.g., such as heating envelope 430 described above with respect to FIG. 5) and bending device may be such as bending device 600 described above with respect to FIGS. 7A-7E or bending device 700 described above with respect to FIGS. 8B-8E.

In some embodiments, at least one of the heating device and the bending device may be not sterile. In this case, the elongated assembly may include an envelope (e.g., such as envelope 330, 340, 350 described above with respect to FIGS. 4A, 4B and 4C, respectively) that at least partly envelopes sterile elongated orthopedic implant at least partly surrounded by sterile transverse cross-sectional profile maintaining device.

Advantageously, the disclosed devices, assemblies, kits, systems and methods for shaping of elongated elements containing thermoplastic polymers may enable shaping of the elongated elements containing thermoplastic elements while preventing distortion of the shape of the cross-sectional profile in the shaping region. Furthermore, the disclosed devices and systems may be located in the operation room and may enable shaping of the elongated elements thereof in the operation room during the operational procedure.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of bending of an elongated assembly, the method comprising:
   providing an elongated assembly, the elongated assembly having a length and comprising:
      an elongated orthopedic implant comprising a thermoplastic polymer, and
      a transverse cross-sectional profile maintaining device surrounding completely and supporting the elongated orthopedic implant along the entire length of the elongated orthopedic implant, such that the transverse cross-sectional profile maintaining device maintains a shape and prevents distortion of a transverse cross-sectional profile of the elongated orthopedic implant during shaping upon heating of the elongated assembly,
   heating the elongated assembly using a heating device to provide a heated elongated assembly;
   configuring a bending device according to a desired bending profile of the elongated orthopedic implant;
      bending the heated elongated assembly by the bending device to provide a bended elongated assembly comprising a bended elongated orthopedic implant having the desired bending profile while maintaining the shape and preventing the distortion of the transverse cross-sectional profile of the elongated orthopedic implant by the transverse cross-sectional profile maintaining device;
      cooling the bended elongated assembly; and
      releasing the transverse cross-sectional profile maintaining device from the elongated orthopedic implant.

2. The method of claim 1, wherein the elongated assembly, the heating device and the bending device are sterile.

3. The method of claim 1, wherein at least one of the heating device and the bending device is not sterile, and wherein the elongated assembly comprises an envelope that envelopes the sterile elongated orthopedic implant surrounded by sterile transverse cross-sectional profile maintaining device.

4. The method of claim 1, wherein the transverse cross-sectional profile maintaining device comprises:
   multiple coils adjacently arranged along a longitudinal axis of the device and helically connected with each other, wherein the coils are adapted to surround and tightly support at least a portion of the elongated orthopedic implant and are unwindably removable from the elongated orthopedic implant upon the shaping thereof.

5. The method of claim 3, wherein the envelope comprises one or more caps each adapted to close one end of the envelope.

6. The method of claim 5, wherein at least one cap of the one or more caps is screwable to the respective end of the envelop.

* * * * *